US012399164B2

(12) United States Patent
Smith et al.

(10) Patent No.: US 12,399,164 B2
(45) Date of Patent: Aug. 26, 2025

(54) EMISSIONS ESTIMATE MODEL ALGORITHMS AND METHODS

(71) Applicant: SeekOps Inc., Austin, TX (US)

(72) Inventors: Brendan James Smith, Lakeway, TX (US); Anders Andelman Nottrott, Santa Barbara, CA (US); Andrew David Aubrey, Austin, TX (US); Stuart Buckingham, Austin, TX (US)

(73) Assignee: SeekOps Inc., Austin, TX (US)

( * ) Notice: Subject to any disclaimer, the term of this patent is extended or adjusted under 35 U.S.C. 154(b) by 723 days.

(21) Appl. No.: 17/125,863

(22) Filed: Dec. 17, 2020

(65) Prior Publication Data

US 2021/0140934 A1 May 13, 2021

Related U.S. Application Data

(63) Continuation-in-part of application No. 16/972,156, filed as application No. PCT/US2019/038011 on Jun. 19, 2019.

(Continued)

(51) Int. Cl.
*G01N 33/00* (2006.01)
*B64U 101/35* (2023.01)
(Continued)

(52) U.S. Cl.
CPC ....... *G01N 33/0073* (2013.01); *G05D 1/0022* (2013.01); *G05D 1/0094* (2013.01);
(Continued)

(58) Field of Classification Search
CPC ............ G01N 33/0062; G01N 33/0047; B64C 39/024; B64D 47/00; H04L 5/0044;
(Continued)

(56) References Cited

U.S. PATENT DOCUMENTS

| 3,780,566 A | 12/1973 | Smith et al. |
| 4,135,092 A * | 1/1979 | Milly .................. G01N 1/2273 |
| | | 250/338.5 |

(Continued)

FOREIGN PATENT DOCUMENTS

| AU | 3401499 A | 11/1999 |
| CN | 101470072 A | 7/2009 |

(Continued)

OTHER PUBLICATIONS

1 International Search Report and Written Opinion for PCT/US19/38011 mailed Sep. 9, 2019.

(Continued)

*Primary Examiner* — Douglas Kay
(74) *Attorney, Agent, or Firm* — Command IP LLP; Michael Zarrabian

(57) ABSTRACT

Systems, devices, and methods including a processor having addressable memory, the processor configured to: receive a trace-gas data packet, where the trace-gas data packet comprises a trace-gas concentration data from a trace-gas sensor and a location data for the trace-gas sensor from a location sensor, where the location data for the trace-gas sensor comprises a trajectory of the trace-gas sensor in space; receive at least one Meteorological data packet from one or more weather stations, where each weather station is distal from the trace-gas sensor, where each weather station generates a corresponding Meteorological data packet, where each Meteorological data packet comprises weather data; combine the trace-gas data packet with a selected spatial and temporal Meteorological data packet; and determine a trace-gas emission rate of a trace-gas source based on the combined trace-gas data packet and the selected Meteorological data packet.

18 Claims, 28 Drawing Sheets

US 12,399,164 B2
Page 2

Related U.S. Application Data

(60) Provisional application No. 62/949,309, filed on Dec. 17, 2019, provisional application No. 62/687,147, filed on Jun. 19, 2018.

(51) Int. Cl.
| | |
|---|---|
| *G05D 1/00* | (2024.01) |
| *G06V 20/10* | (2022.01) |
| *G06V 20/13* | (2022.01) |
| *G06V 20/17* | (2022.01) |
| *G08G 5/26* | (2025.01) |
| *G08G 5/30* | (2025.01) |
| *B64U 101/30* | (2023.01) |

(52) U.S. Cl.
CPC ............. *G05D 1/106* (2019.05); *G06V 20/10* (2022.01); *G06V 20/13* (2022.01); *G06V 20/17* (2022.01); *G08G 5/26* (2025.01); *G08G 5/30* (2025.01); *B64U 2101/30* (2023.01); *B64U 2101/35* (2023.01)

(58) Field of Classification Search
CPC ................ B64U 10/13; B64U 2201/20; B64U 2101/00; B64U 2201/10
See application file for complete search history.

(56) References Cited

U.S. PATENT DOCUMENTS

| | | |
|---|---|---|
| 4,233,564 A | 11/1980 | Kerbel |
| 4,507,558 A | 3/1985 | Bonne |
| 4,651,010 A | 3/1987 | Javan |
| 4,988,833 A | 1/1991 | Lai |
| 5,047,639 A | 9/1991 | Wong |
| 5,075,619 A | 12/1991 | Said |
| 5,173,749 A | 12/1992 | Tell et al. |
| 5,291,265 A | 3/1994 | Kebabian |
| 5,317,156 A | 5/1994 | Cooper et al. |
| 5,767,780 A | 6/1998 | Smith et al. |
| 5,822,058 A | 10/1998 | Adler-Golden et al. |
| 6,064,488 A | 5/2000 | Brand et al. |
| 6,295,859 B1 | 10/2001 | Hayden et al. |
| 6,356,350 B1 | 3/2002 | Silver et al. |
| 6,509,566 B1 | 1/2003 | Wamsley et al. |
| 6,549,630 B1 | 4/2003 | Bobisuthi |
| 7,162,933 B2 | 1/2007 | Thompson et al. |
| 7,800,751 B1 | 9/2010 | Silver et al. |
| 7,833,480 B2 | 11/2010 | Blazewicz et al. |
| 8,060,270 B2 | 11/2011 | Vian et al. |
| 8,294,899 B2 | 10/2012 | Wong |
| 8,451,120 B2 | 5/2013 | Johnson, Jr. et al. |
| 8,730,461 B2 * | 5/2014 | Andreussi .......... G01N 21/3103 356/72 |
| 9,183,371 B2 | 11/2015 | Narendra et al. |
| 9,183,731 B1 | 11/2015 | Bokhary |
| 9,235,974 B2 | 1/2016 | Johnson, Jr. et al. |
| 9,250,175 B1 | 2/2016 | McManus |
| 9,494,511 B2 | 11/2016 | Wilkins |
| 9,599,529 B1 | 3/2017 | Steele et al. |
| 9,599,597 B1 | 3/2017 | Steele et al. |
| 10,023,311 B2 | 7/2018 | Lai et al. |
| 10,023,323 B1 | 7/2018 | Roberts et al. |
| 10,031,040 B1 | 7/2018 | Smith et al. |
| 10,126,200 B1 | 11/2018 | Steele et al. |
| 10,268,198 B2 | 4/2019 | Mantripragada et al. |
| 10,325,485 B1 | 6/2019 | Schuster |
| 10,365,646 B1 | 7/2019 | Farnsworth et al. |
| 10,429,546 B1 | 10/2019 | Ulmer |
| 10,677,771 B2 | 6/2020 | Dittberner et al. |
| 10,753,864 B2 | 8/2020 | Kasten et al. |
| 10,816,458 B2 | 10/2020 | Kasten et al. |
| 10,830,034 B2 | 11/2020 | Cooley et al. |
| 10,962,437 B1 | 3/2021 | Nottrott et al. |
| 11,105,784 B2 | 8/2021 | Kukreja et al. |
| 11,112,308 B2 | 9/2021 | Kreitinger et al. |
| 11,275,068 B2 | 3/2022 | Willett |
| 11,299,268 B2 | 4/2022 | Christensen et al. |
| 11,519,855 B2 | 12/2022 | Black et al. |
| 11,557,212 B2 | 1/2023 | Hong |
| 11,614,430 B2 | 3/2023 | Buckingham et al. |
| 11,619,562 B2 | 4/2023 | Leen et al. |
| 11,710,411 B2 | 7/2023 | Van Meeteren et al. |
| 11,748,866 B2 | 9/2023 | Vargas |
| 12,015,386 B2 | 6/2024 | Gatabi et al. |
| 2002/0005955 A1 | 1/2002 | Kramer et al. |
| 2003/0160174 A1 | 8/2003 | Grant et al. |
| 2003/0189711 A1 | 10/2003 | Orr et al. |
| 2003/0230716 A1 | 12/2003 | Russell et al. |
| 2004/0012787 A1 | 1/2004 | Galle et al. |
| 2004/0017762 A1 | 1/2004 | Sogawa et al. |
| 2004/0212804 A1 | 10/2004 | Neff et al. |
| 2006/0015290 A1 | 1/2006 | Warburton et al. |
| 2006/0044562 A1 | 3/2006 | Hagene et al. |
| 2006/0232772 A1 | 10/2006 | Silver |
| 2006/0234621 A1 | 10/2006 | Desrochers et al. |
| 2007/0137318 A1 | 6/2007 | Desrochers et al. |
| 2008/0169934 A1 | 7/2008 | Lang et al. |
| 2008/0243372 A1 | 10/2008 | Bodin et al. |
| 2009/0201507 A1 | 8/2009 | Kluczynski et al. |
| 2009/0263286 A1 | 10/2009 | Isomura et al. |
| 2009/0326792 A1 * | 12/2009 | McGrath ................. G01W 1/08 701/4 |
| 2010/0004798 A1 | 1/2010 | Bodin et al. |
| 2010/0131207 A1 * | 5/2010 | Lippert ................... G01S 17/95 702/49 |
| 2010/0140478 A1 | 6/2010 | Wilson et al. |
| 2010/0147081 A1 | 6/2010 | Thomas |
| 2011/0035149 A1 | 2/2011 | McAndrew et al. |
| 2011/0074476 A1 | 3/2011 | Heer et al. |
| 2011/0150035 A1 | 6/2011 | Hanson et al. |
| 2011/0164251 A1 | 7/2011 | Richter |
| 2011/0213554 A1 | 9/2011 | Archibald et al. |
| 2011/0242659 A1 | 10/2011 | Eckles et al. |
| 2011/0257944 A1 | 10/2011 | Du et al. |
| 2012/0120397 A1 | 5/2012 | Furtaw et al. |
| 2013/0044314 A1 | 2/2013 | Koulikov et al. |
| 2013/0061692 A1 | 3/2013 | Muresan et al. |
| 2013/0076900 A1 | 3/2013 | Mrozek et al. |
| 2013/0208262 A1 * | 8/2013 | Andreussi ............... G01M 3/38 356/72 |
| 2014/0172323 A1 | 6/2014 | Marino |
| 2014/0204382 A1 | 7/2014 | Christensen |
| 2014/0236390 A1 | 8/2014 | Mohamadi |
| 2014/0336957 A1 | 11/2014 | Hanson et al. |
| 2015/0039256 A1 | 2/2015 | Michalske |
| 2015/0072633 A1 | 3/2015 | Massarella et al. |
| 2015/0145954 A1 | 5/2015 | Pulleti et al. |
| 2015/0226575 A1 | 8/2015 | Rambo |
| 2015/0275114 A1 | 10/2015 | Tumiatti et al. |
| 2015/0295543 A1 | 10/2015 | Brown et al. |
| 2015/0316473 A1 | 11/2015 | Kester et al. |
| 2015/0323449 A1 | 11/2015 | Jones et al. |
| 2015/0336667 A1 | 11/2015 | Srivastava et al. |
| 2016/0018373 A1 | 1/2016 | Pagé et al. |
| 2016/0070265 A1 | 3/2016 | Liu et al. |
| 2016/0104250 A1 | 4/2016 | Allen et al. |
| 2016/0146696 A1 | 5/2016 | Steele et al. |
| 2016/0161456 A1 | 6/2016 | Risk et al. |
| 2016/0202225 A1 | 7/2016 | Feng et al. |
| 2016/0214715 A1 * | 7/2016 | Meffert ................... G01S 17/88 |
| 2016/0216172 A1 | 7/2016 | Rella et al. |
| 2016/0307447 A1 | 10/2016 | Johnson et al. |
| 2016/0357192 A1 | 12/2016 | McGrew et al. |
| 2017/0003684 A1 | 1/2017 | Knudsen et al. |
| 2017/0057081 A1 | 3/2017 | Krohne et al. |
| 2017/0089829 A1 | 3/2017 | Bartholomew et al. |
| 2017/0093122 A1 | 3/2017 | Bean et al. |
| 2017/0097274 A1 | 4/2017 | Thorpe et al. |
| 2017/0115218 A1 | 4/2017 | Huang et al. |
| 2017/0134497 A1 | 5/2017 | Harter et al. |
| 2017/0158353 A1 | 6/2017 | Schmick |
| 2017/0199647 A1 | 7/2017 | Richman et al. |
| 2017/0206648 A1 | 7/2017 | Marra et al. |

(56) References Cited

U.S. PATENT DOCUMENTS

| | | |
|---|---|---|
| 2017/0235018 A1 | 8/2017 | Foster et al. |
| 2017/0259920 A1* | 9/2017 | Lai ..................... G05D 1/0011 |
| 2017/0290034 A1 | 10/2017 | Desai et al. |
| 2017/0307519 A1 | 10/2017 | Black et al. |
| 2017/0336281 A1 | 11/2017 | Waxman et al. |
| 2018/0023974 A1 | 1/2018 | Otani et al. |
| 2018/0024091 A1 | 1/2018 | Wang et al. |
| 2018/0045561 A1 | 2/2018 | Leen et al. |
| 2018/0045596 A1 | 2/2018 | Prasad et al. |
| 2018/0050798 A1 | 2/2018 | Kapuria |
| 2018/0059003 A1 | 3/2018 | Jourdainne et al. |
| 2018/0067066 A1 | 3/2018 | Giedd et al. |
| 2018/0095478 A1 | 4/2018 | van Cruyningen |
| 2018/0109767 A1 | 4/2018 | Li et al. |
| 2018/0122246 A1 | 5/2018 | Clark |
| 2018/0127093 A1 | 5/2018 | Christensen et al. |
| 2018/0188129 A1 | 7/2018 | Choudhury et al. |
| 2018/0209902 A1 | 7/2018 | Myshak et al. |
| 2018/0259955 A1 | 9/2018 | Noto |
| 2018/0266241 A1 | 9/2018 | Ferguson et al. |
| 2018/0266946 A1 | 9/2018 | Kotidis et al. |
| 2018/0284088 A1 | 10/2018 | Verbeck, IV |
| 2018/0292374 A1 | 10/2018 | Dittberner et al. |
| 2018/0321692 A1 | 11/2018 | Castillo-Effen et al. |
| 2018/0322699 A1 | 11/2018 | Gray et al. |
| 2019/0011920 A1 | 1/2019 | Heinonen et al. |
| 2019/0011935 A1 | 1/2019 | Ham et al. |
| 2019/0025199 A1 | 1/2019 | Koulikov |
| 2019/0033194 A1 | 1/2019 | DeFreez et al. |
| 2019/0049364 A1 | 2/2019 | Rubin |
| 2019/0066479 A1 | 2/2019 | Wesley et al. |
| 2019/0077506 A1 | 3/2019 | Shaw et al. |
| 2019/0086202 A1 | 3/2019 | Guan et al. |
| 2019/0095687 A1 | 3/2019 | Shaw et al. |
| 2019/0154874 A1* | 5/2019 | Shams ................. B64C 1/0009 |
| 2019/0178743 A1 | 6/2019 | McNeil |
| 2019/0195789 A1 | 6/2019 | Pan et al. |
| 2019/0204189 A1 | 7/2019 | Mohr, Jr. et al. |
| 2019/0212419 A1 | 7/2019 | Jeong et al. |
| 2019/0220019 A1 | 7/2019 | Tan et al. |
| 2019/0228573 A1 | 7/2019 | Sen et al. |
| 2019/0234868 A1 | 8/2019 | Tanomura et al. |
| 2019/0331652 A1 | 10/2019 | Ba et al. |
| 2020/0050189 A1 | 2/2020 | Gu et al. |
| 2020/0065433 A1 | 2/2020 | Duff et al. |
| 2020/0109976 A1 | 4/2020 | Ajay et al. |
| 2020/0135036 A1 | 4/2020 | Campbell |
| 2020/0182779 A1 | 6/2020 | Kasten et al. |
| 2020/0249092 A1 | 8/2020 | Podmore et al. |
| 2020/0309690 A1 | 10/2020 | Green et al. |
| 2020/0373172 A1 | 11/2020 | Suzuki |
| 2020/0400635 A1 | 12/2020 | Potyrailo et al. |
| 2021/0017926 A1 | 1/2021 | Alkadi et al. |
| 2021/0037197 A1 | 2/2021 | Kester et al. |
| 2021/0055180 A1 | 2/2021 | Thorpe et al. |
| 2021/0109074 A1* | 4/2021 | Smith ................. G01N 33/0062 |
| 2021/0140934 A1* | 5/2021 | Smith ................. G05D 1/0094 |
| 2021/0190745 A1 | 6/2021 | Buckingham et al. |
| 2021/0190918 A1 | 6/2021 | Li et al. |
| 2021/0199565 A1 | 7/2021 | John et al. |
| 2021/0247369 A1* | 8/2021 | Nottrott ................. B64C 39/024 |
| 2021/0255158 A1* | 8/2021 | Smith ................... B64D 47/00 |
| 2021/0300591 A1 | 9/2021 | Tian |
| 2021/0321174 A1 | 10/2021 | Sun et al. |
| 2021/0364427 A1 | 11/2021 | Smith et al. |
| 2021/0382475 A1 | 12/2021 | Smith et al. |
| 2022/0082495 A1 | 3/2022 | Kreitinger et al. |
| 2022/0113290 A1 | 4/2022 | Smith et al. |
| 2022/0170810 A1 | 6/2022 | Miller, II et al. |
| 2022/0341806 A1 | 10/2022 | Miller et al. |
| 2022/0357231 A1 | 11/2022 | Nahata et al. |
| 2023/0194487 A1 | 6/2023 | Buckingham et al. |
| 2023/0213413 A1 | 7/2023 | Mohr, Jr. et al. |
| 2023/0274651 A1 | 8/2023 | McGuire et al. |
| 2023/0392498 A1 | 12/2023 | Srivastav et al. |

FOREIGN PATENT DOCUMENTS

| | | |
|---|---|---|
| CN | 104458588 A | 3/2015 |
| CN | 205749271 U | 11/2016 |
| CN | 106568516 A | 4/2017 |
| CN | 106769977 A | 5/2017 |
| CN | 107703075 A | 2/2018 |
| CN | 109780452 A | 5/2019 |
| CN | 211508182 U | 9/2020 |
| CN | 112213443 A | 1/2021 |
| DE | 29601472 U1 | 5/1996 |
| DE | 69333010 | 4/2004 |
| DE | 102014013822 A1 | 3/2016 |
| EP | 0450809 A2 | 10/1991 |
| EP | 1371962 B1 | 7/2011 |
| EP | 3339855 A1 | 6/2018 |
| FR | 3047073 A1 | 7/2017 |
| FR | 3047073 B1 | 8/2019 |
| GB | 2538563 A | 11/2016 |
| JP | H08247939 A | 9/1996 |
| JP | 200975823 A | 4/2009 |
| KR | 20170062813 A | 6/2017 |
| KR | 101770254 B1 | 8/2017 |
| TW | 522226 B | 3/2003 |
| WO | 1999054700 A2 | 10/1999 |
| WO | 02066950 A1 | 8/2002 |
| WO | 2008021311 A2 | 2/2008 |
| WO | 2015073687 A1 | 5/2015 |
| WO | 2016045791 A1 | 3/2016 |
| WO | 2016162673 A1 | 10/2016 |
| WO | 2017069979 A1 | 4/2017 |
| WO | 2018121478 A1 | 7/2018 |
| WO | 2018227153 A1 | 12/2018 |
| WO | 2019246280 A1 | 12/2019 |
| WO | 2020027684 A1 | 1/2020 |
| WO | 2020028353 A1 | 2/2020 |
| WO | 2020086499 A1 | 4/2020 |
| WO | 2020206006 A1 | 10/2020 |
| WO | 2020206008 A1 | 10/2020 |
| WO | 2020206020 A1 | 10/2020 |
| WO | 2021055902 A1 | 3/2021 |
| WO | 2021158916 A1 | 8/2021 |
| WO | 2022093864 A1 | 5/2022 |
| WO | 2022211837 A1 | 10/2022 |

OTHER PUBLICATIONS

U.S. Appl. No. 62/687,147, filed Jun. 19, 2018, Brendan James Smith.

"Safesite Multi-Threat Detection System", Jul. 11, 2012 (Jul. 11, 2012), pp. 1-6, XP055245980.

International Search Report and Written Opinion for PCT/US19/38015, mailed Oct. 18, 2019.

International Search Report and Written Opinion for PCT/US19/44119, mailed Oct. 17, 2019.

International Search Report and Written Opinion for PCT/US20/26228 mailed Jul. 1, 2020.

International Search Report and Written Opinion for PCT/US20/26232 mailed Jun. 26, 2020.

International Search Report and Written Opinion for PCT/US20/26246 mailed Jun. 29, 2020.

International Search Report and Written Opinion for PCT/US20/51696, mailed Feb. 3, 2021.

International Search Report and Written Opinion for PCT/US2020/044978, mailed Oct. 26, 2020.

International Search Report and Written Opinion for PCT/US2021/016821 mailed Apr. 26, 2021.

International Search Report and Written Opinion for PCT/US2021/024177, mailed Jun. 23, 2021.

International Search Report and Written Opinion for PCT/US2021/056708, mailed Jan. 27, 2022.

International Search Report and Written Opinion for PCT/US21/42061, mailed Nov. 26, 2021.

International Search Report and Written Opinion for PCT/US21/44532, mailed Jan. 11, 2022.

(56) References Cited

OTHER PUBLICATIONS

International Search Report and Written Opinion for PCT/US21/56710, mailed Feb. 23, 2022.
International Search Report and Written Opinion of PCT/US19/57305, mailed Jan. 2, 2020.
International Search Report and Written Opinion of PCT/US20/54117, mailed Dec. 22, 2020.
Joly, "Atmospheric Measurements by Ultra-Light Spectrometer (AMULSE) Dedicated to Vertical Profile In Situ Measurements of Carbon Dioxide (CO2) Under Weather Balloons: Instrumental Development and Field Application," Sensors 2016, 16, 1609.
Khan, "Low Power Greenhouse Gas Sensors for Unmanned Aerial Vehicles", Remote Snse. 2012, 4, 1355-1368.
Villa. "An Overview of Small Unmanned Aerial Vehicles for Air Quality Measurements: Present Applications and Future Prospectives". Sensors. Web . Jul. 12, 2016.
White, "Development of an Unmanned Aerial Vehicle for the Measurement of Turbulence in the Atmospheric Boundary Layer", Atmosphere, v.8, issue 10, 195, pp. 1-25.
Lilian Joly, The evolution of AMULSE (Atmospheric Measurements by Ultra-Light Spectrometer) and its interest in atmospheric applications. Results of the Atmospheric Profiles of Greenhouse gasEs (APOGEE) weather balloon release campaign for satellite retrieval validation, p. 1-28, Sep. 25, 2019, Atmospheric Measurement Techniques Discussion (Joly).
International Search Report and Written Opinion for PCT/US22/38951, mailed Nov. 28, 2022.
Kelly J F et al. "A capillary absorption spectrometer for stable carbon isotope ratio (C/C) analysis in very small samples", Review of Scientific Instruments, American Institute of Physics, 2 Huntington Quadrangle, Melville, NY 11747, vol. 83, No. 2, Feb. 1, 2012 (Feb. 1, 2012), pp. 23101-23101, XP012161835, ISSN: 0034-6748, DOI: 10.1063/1.3680593.
Krings et al., Atmos. Meas. Tech., 11, 721-739, Feb. 7, 2018.
International Search Report and Written Opinion for PCT/US23/13893, mailed Jun. 30, 2023.
Clilverd, mark A. et al., Energetic particle injection, acceleration, and loss during the geomagnetic disturbances which upset Galaxy 15, Journal of Geophysical Research, vol. 117, A12213, doi: 10.1029/2012JA018175, 2012, pp. 1-16 (Year:2012).
Kem, Christoph et al., Spatial Distribution of Halogen Oxides in the Plume of Mount Pagan Volcano, Mariana Islands, Geophysical Research Letters 10.1029/2018GL079245, Sep. 27, 2018, pp. 9588-9596 (Year:2018).
Liao, J. et al. Observations of Inorganic bromine(HOBr, BrO, and Br2) speciation at Barrow, Alaska in spring 2009, Journal of Geophysical Research, vol. 117, D00R16, doi:10.1029/2011JD016641, 2012, pp. 1-11 (Year:2012).
Liu, Siwen et al., Development of a UAV-Based System to Monitor Air Quality over an Oil Field, Montana Technological University, Montana tech Library Digital Commons @ Montana Tech Graduate Theses & Non-Theses, Fall 2018, pp. 1-85 (Year:2018).
Miyama, Toru et al., Estimating allowable carbon emission for CO2 concentration stabilization using a GCM-based Earth system model, Geophysical Research Letters, vol. 36,L19709, doi:10.1029/2009GL039678, 2009, pp. 0094-8276 (Year:2009).
Oppenheimer Clive et al., Ultraviolet Sensing of Volcanic Sulfur Emissions, Elements (An Internatioknal Magazine of Mineralogy, Geochemistry, and Petrology), Apr. 2010, vol. 6, pp. 87-92 (Year: 2010).
Parazoo, Nicholas C. et al., Interpreting seasonal changes in the carbon balance of southern Amazonia using measurements of XCO2 and chlorophyll fluorescence from GOSAT, Geophysical Research Letters, vol. 40.2829-2833, doi: 10.1002/grl.50452, 2013 pp. 0 2829-2833 (Year:2013).
Queiber, Manuel et al., A new frontier in CO2 flux measurements using a highly portable DIAL laser system, Scientific Reports, DOI: 10.1038/srep33834 1, Sep. 22, 2016, pp. 1-13(Year:2016).
Queiber, Manuel et al., Large-area quantification of subaerial CO2 anomalies with portable laser remote sensing and 2d tomography, The Leading Edge Mar. 2018, pp. 306-313 (Year:2018).
International Search Report and Written Opinion for PCT/US23/23905 mailed Oct. 5, 2023.
International Search Report and Written Opinion for PCT/US2023/023933 mailed Sep. 26, 2023.
Development of a mobile tracer correlation method for assessment of air emissions from landfills and other area sources, Atmospheric Environment 102 (2015) 323-330. T.A. Foster-Wittig et al. 2015.
Measurements of Methane Emissions from Landfills Using a Time Correlation Tracer Method Based on FTIR Absorption Spectroscopy, Environ. Sci. Technol. 2001, 35, 21-25, B. Galle et al. 2001.
IEEE Conference Paper, "Research of the high pressure jet performance of small size nozzle," ISBN :978-1-5090-1087-5, Publication Date : Oct. 1, 2016, Conference dates Oct. 10, 2016 thru Oct. 12, 2016.[retrieved from the Internet] on Sep. 1, 2023 at 4:14pm.
Tao Lei et al:"Low-power, open-path mobile sensing platform for high—resolution measurements of greenhouse gases and air pollutants", Applied Physics B, Springer Berlin Heidelberg, Berlin/Heidelberg, vol. 119, No. 1, Mar. 10, 2015 (Mar. 10, 2015), pp. 153-164, XP035445836, ISSN: 0946-2171, DOI:10.1007/ S00340-015-6069-1 [retrieved on Mar. 10, 2015].
Tarsitano C G et al: Multilaser Herriott Cell for Planetary Tunable Laser Spectrometers', Applied Optics , Optical Society of America, Washington, DC, US, vol. 46, No. 28, Oct. 1, 2007 (Oct. 1, 2007), pp. 6923-6935, XP001508502, ISSN:0003-6935, DOI: 10.1364/AO.46.006923.
Adame J A et al: "Application of cluster analysis to surface ozone, NOand SOdaily patterns in an industrial area in Central-Southern Spain measured with a DOAS system", Science of the Total Environment, Elsevier, Amsterdam, NL, vol. 429, Apr. 11, 2012 (Apr. 11, 2012), pp. 281-291, XP028491183, ISSN: 0048-9697, DOI: 10.1016/J.SCITOTENV.2012.04.032.
Coombes et al, "Optimal Polygon Decomposition for UAV Survey Coverage Path Planning in Wind", published: Jul. 2018, publisher: 'Sensors' (Year:2018).
He et al. "Static Targets' Track Path for UAVs Meeting the Revisit Interval Requirement", published :2013, publisher : IEEE (Year:2013).
Uehara, K: "Dependence of harmonic signals 1-15 on sample-gas parameters in wavelength-modulation spectroscopy for precise absorption measurements", Applied Physics B, Springer Berlin Heidelberg, Berlin/Heidelberg, vol. 67, Jan. 2, 1998, pp. 517-523, XP007921671, ISSN:0946-2171, DOI: 10.1007/ S003400050537.
Day, S., and et al. "Characterisation of regional fluxes of methane in the Surat Basin, Queensland, Phase 1: A review and analysis of literature on methane detection and flux determination." (2013) (Year: 2013).
Field Trial of Methane Emission Quantification Technologies, Society of Petroleum Engineers, SPE-201537-MS, Allen et al., Oct. 2020.
Feng, Lingbing, Nowak, Gen, O'Neill, T.J., Welsh, A.H."Cutoff; A spatio-temporal imputation method." Journal of Hydrology 519 (2014) : 3591-3605 (Year:2014).
Cabreira et al. "Survey on Coverage Path Planning with Unmanned Aerial Vehicles", published: Drones, published: Jan. 2019, pp. 1-38, year 2019.
Feitz Andrew et al: "The Ginninderra CH4 and CO2 release experiment: An evaluation of gas detection and quantification techniques", International Journal of Greenhouse Gas Control, Elsevier, Amsterdam, NL, vol. 70, Mar. 15, 2018 (Mar. 15, 2018), pp. 202-224, XP085368237, ISSN: 1750-5836, DOI: 10.1016/J.IJGGC.2017.11.018.
Jensen Morten Bang et al: "Quantification of greenhouse gas emissions from a biological waste treatment facility", Waste Management, Elsevier, New York, NY, US, vol. 67, May 29, 2017 (May 29, 2017), pp. 375-384, XP085157318, ISSN: 0956-053X, DOI: 10.1016/J.WASMAN.2017.05.033.
Mohn Joachim et al: "A dual tracer ratio method for comparative emission measurements in an experimental dairy housing", Atmospheric Environment, Elsevier, Amsterdam, NL, vol. 179, Feb. 1,

(56) References Cited

OTHER PUBLICATIONS 2018 (Feb. 1, 2018), pp. 12-22, XP085370597, ISSN: 1352-2310, DOI: 10.1016/J.ATMOSENV.2018.01.057.

* cited by examiner

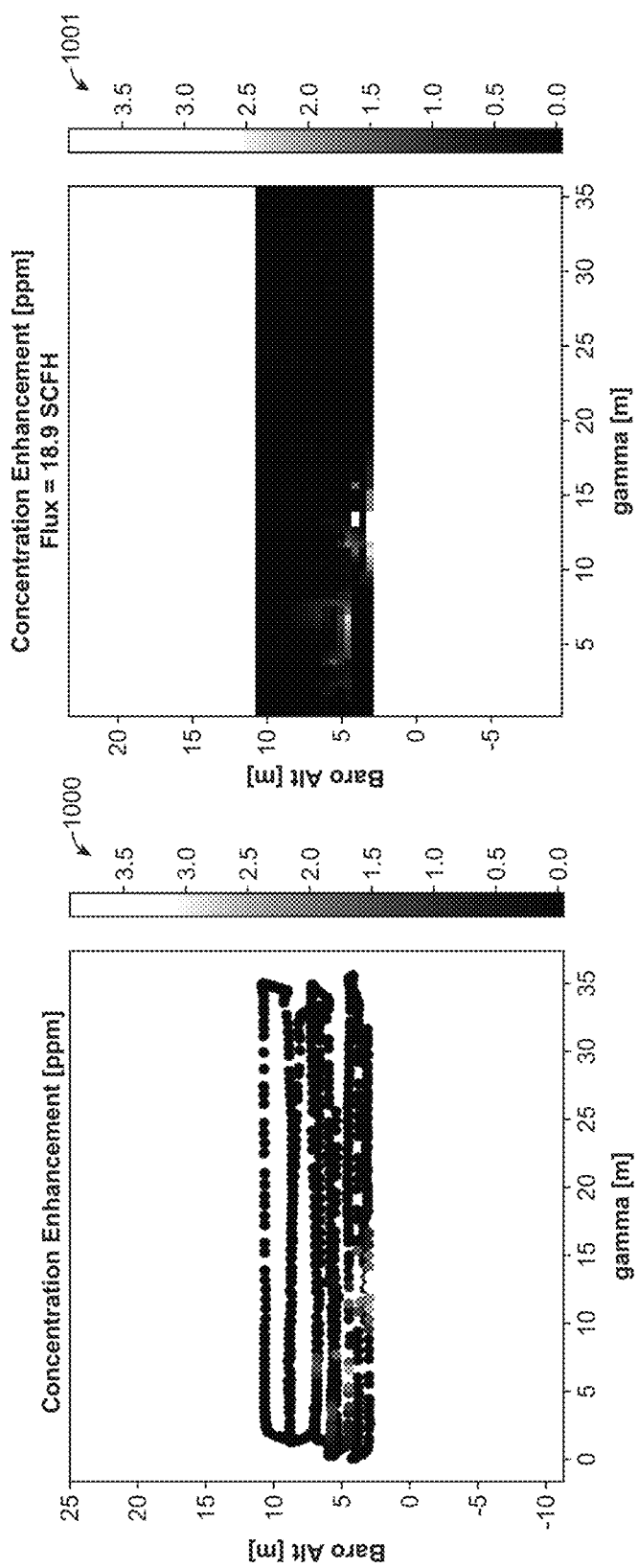

EMISSIONS ESTIMATE MODEL ALGORITHMS AND METHODS

CROSS-REFERENCE TO RELATED APPLICATIONS

This application is a continuation-in-part of U.S. Non-Provisional patent application Ser. No. 16/972,156, filed Dec. 4, 2020, which is a 35 U.S.C § 371 National Stage Entry of International Application No. PCT/US2019/038011 filed Jun. 19, 2019, which claims the priority benefit of U.S. Provisional Patent Application Ser. No. 62/687,147 filed Jun. 19, 2018, and this application claims the priority benefit of U.S. Provisional Patent Application Ser. No. 62/949,309 filed Dec. 17, 2019, all of which are incorporated herein by reference in their entirety for all purposes.

FIELD OF ENDEAVOR

Embodiments relate generally to trace-gas concentration measurement, and more particularly to Unmanned Aerial System (UAS) trace-gas concentration measurement.

BACKGROUND

Methane ($CH_4$) is an odorless and colorless naturally occurring organic molecule, which is present in the atmosphere at average ambient levels of approximately 1.85 ppm as of 2018 and is projected to continually climb. While methane is found globally in the atmosphere, a significant amount is collected or "produced" through anthropogenic processes including exploration, extraction, and distribution of petroleum in the form of natural gas. Natural gas, an odorless and colorless gas, is a primary source of energy used to produce electricity and heat. The main component of natural gas is methane (93.9 mol % $CH_4$ typ.). While extraction of natural gas is a large source of methane released to atmosphere, major contributors of methane also include livestock farming (enteric fermentation), and solid waste and wastewater treatment (anaerobic digestion).

SUMMARY

In one embodiment, a system disclosed herein may include: a processor having addressable memory, the processor configured to: receive an unmanned aerial vehicle (UAV) data packet, where the UAV data packet comprises trace-gas concentration data and UAV information from a UAV flight path; receive at least one Meteorological data packet, where the Meteorological data packet comprises weather data; combine the UAV data packet with a nearest Meteorological data packet; and determine a trace-gas emission rate of a trace-gas source based on the combined UAV data packet and the nearest Meteorological data packet.

Additional system embodiments may include: a display in communication with the processor, where the display may be configured to show the determined trace-gas emission rate of the trace-gas source on a map. In additional system embodiments, the map may be at least one of: a satellite image, an aerial image, a two-dimensional color map, a two-dimensional contour map, and a three-dimensional topographical surface.

In additional system embodiments, the processor may be further configured to: determine the UAV flight path. In additional system embodiments, the UAV flight path may be a raster grid flight path downwind of the trace-gas source. In additional system embodiments, the UAV flight path may form a flight plane substantially perpendicular to a ground surface and an average wind direction. In additional system embodiments, the flightpath may be any flight path that intersects the area downstream of the leak source and varies in horizontal distance perpendicular to the axis of the wind direction and altitude.

Additional system embodiments may include: a payload of a UAV, where the payload may include one or more gas concentration sensors configured to generate the trace-gas concentration data along the UAV flight path. In additional system embodiments, the UAV information along the UAV flight path may include at least one of: a location of the UAV, a time corresponding to the location of the UAV, a barometric pressure, an altitude, a relative altitude, and an orientation of the UAV, and where the UAV information along the UAV flight path corresponds to the generated trace-gas concentration data along the UAV flight path. In additional system embodiments, the location of the UAV may be determined by at least one of: a global positioning system (GPS), an onboard avionics, and a location sensor. In additional system embodiments, the relative altitude of the UAV may be determined by at least one of: an altitude of a global positioning system (GPS), a LIDAR, a Sonar, a radar, and a barometric pressure sensor. In additional system embodiments, the orientation of the UAV may be determined by at least one of: an inertial measurement unit (IMU) and an orientation sensor.

Additional system embodiments may include: one or more weather stations, where each weather station generates the Meteorological data packet. In additional system embodiments, the Meteorological Data Packet may include data from at least one of: an anemometer, one or more pressure sensors, a pryanometer, a ground temperature sensor, an air temperature sensor, and a current atmospheric condition sensor. In additional system embodiments, at least one of: a ground control station (GCS), a cloud server, the UAV, and the weather station may include the processor. In additional system embodiments, the determined trace-gas emission rate may be stored by at least one of: a ground control station (GCS), a cloud server, and one or more gas concentration sensors.

In another embodiment, a method disclosed herein may include: receiving, by a processor having addressable memory, an unmanned aerial vehicle (UAV) data packet, where the UAV data packet comprises trace-gas concentration data and UAV information from a UAV controller; receiving, by the processor, at least one Meteorological data packet, where the Meteorological data packet comprises weather data; combining, by the processor, the UAV data packet with a nearest Meteorological data packet; and determining, by the processor a trace-gas emission rate of a trace-gas source based on the combined UAV data packet and the nearest Meteorological data packet.

Additional method embodiments may include: determining, by the processor, the UAV flight path, where the UAV flight path may be a raster grid pattern flight path, where the UAV flight path may be downwind of the trace-gas source, and where the UAV flight path forms a flight plane substantially perpendicular to a ground surface and an average wind direction. In additional method embodiments, the UAV flight path may be controlled by a user via a ground control station (GCS).

Additional method embodiments may include: measuring, by a payload of a UAV, the trace-gas concentration data along the UAV flight path, where the payload comprises one or more gas concentration sensors; generating, by the UAV, the UAV data packet, where the UAV data packet comprises a spatial position of the UAV at each trace-gas concentration data measurement; and generating, by a weather station of one or more weather stations, the Meteorological data packet; where the UAV data packet comprises data from at least one of: a weather sensor, an onboard avionics, a barometric pressure sensor, an orientation sensor, an intertial measurement unit (IMU), a wireless radio, a global positioning system (GPS), a time measurement device, an altitude sensor, a location sensor, a radar, a lidar, an anemometer, an a Sonar; and where the Meteorological data packet comprises data from at least one of: an anemometer, one or more pressure sensors, a pryanometer, a ground temperature sensor, an air temperature sensor, and a current atmospheric condition sensor.

In another embodiments, the system disclosed herein may include: an unmanned aerial vehicle configured to generate a UAV data packet; a payload of the UAV, where the payload comprises one or more gas concentration sensors configured to generate the trace-gas concentration data along a UAV flight path; one or more sensors of the UAV, where the one or more sensors of the UAV are configured to generate UAV information; one or more weather stations, where each weather station generates a Meteorological data packet, where the Meteorological data packet comprises weather data from one or more sensors of the weather station; and a processor having addressable memory, the processor in communication with the UAV and the one or more weather stations, where the processor configured to: receive the UAV data packet, where the UAV data packet comprises trace-gas concentration data from the payload and UAV information the one or more sensors of the UAV; receive at least one Meteorological data packet; combine the UAV data packet with a nearest Meteorological data packet; determine a trace-gas emission rate of a trace-gas source based on the combined UAV data packet and the nearest Meteorological data packet; and show the determined trace-gas emission rate of the trace-gas source on a map via a display in communication with the processor.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which:

FIG. 10A depicts projected values along the (y, z) plane, according to one embodiment.

FIG. 10B depicts an averaged and interpolated flux plane, according to one embodiment.

DETAILED DESCRIPTION

Figure 1A:
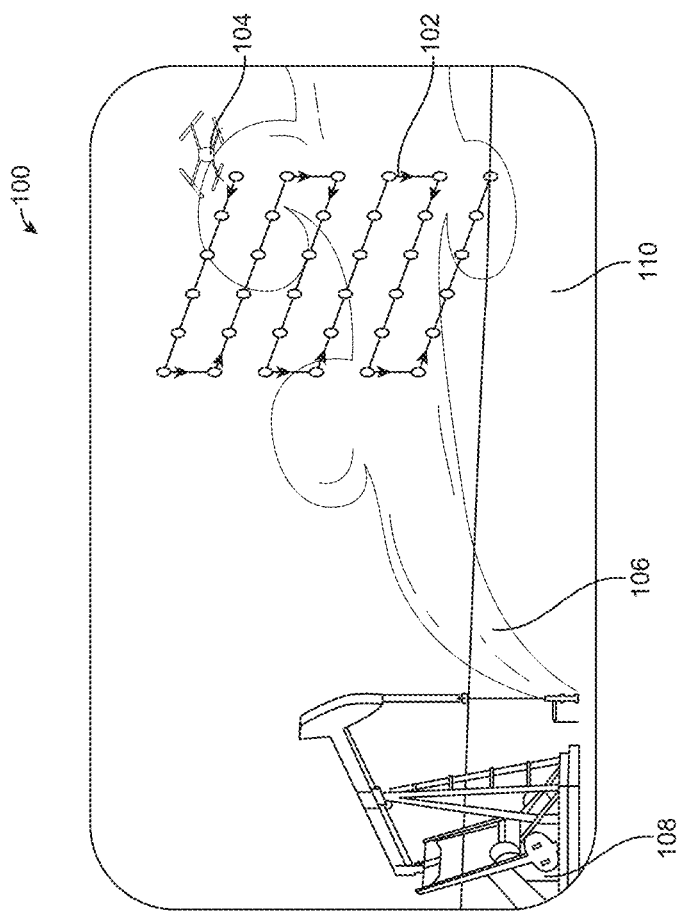
FIG. 1A depicts an illustration of an unmanned aerial system (UAS) emissions measurement process and flight path, according to one embodiment.

The following description is made for the purpose of illustrating the general principles of the embodiments discloses herein and is not meant to limit the concepts disclosed herein. Further, particular features described herein can be used in combination with other described features in each of the various possible combinations and permutations. Unless otherwise specifically defined herein, all terms are to be given their broadest possible interpretation including meanings implied from the description as well as meanings understood by those skilled in the art and/or as defined in dictionaries, treatises, etc.

The present system and method disclosed herein allow for determining a trace-gas emission rate of a trace-gas source based on measurements from one or more sensors mounted on an unmanned aerial vehicle (UAV), UAV data, and one or more sensors from one or more weather stations. The UAV may fly a flight path downwind of the trace-gas source which transects a point downstream of the emission source and varies in the horizontal axis perpendicular to the wind direction and altitude. The path of the flight pattern may be substantially perpendicular to a ground surface and an average wind direction to measure trace-gas emissions downwind of the trace-gas source. Data from the one or more UAV sensors, the UAV data, and the one or more sensors from the one or more weather stations may be combined, stored, processed, and/or filtered to determine the trace-gas emission rate of the trace-gas source.

In additional system embodiments, the flightpath may be any flight path that intersects the area downstream of the leak source and varies in horizontal distance perpendicular to the axis of the wind direction and altitude. The flux can be calculated by flying a spiral pattern around the emission source. The spiral pattern may be neither a raster pattern nor a plane. In some embodiments, the flight path may intersect the plume at different horizontal distances perpendicular to the plume (wind) and altitude.

The goal of the natural gas production and supply chain is to deliver gas from source production areas to endpoint users without undue loss. Product loss in this context amounts to flaring or venting, intentional or otherwise, of natural gas to the atmosphere. Undue product loss results in uncaptured revenue, an increased environmental footprint, and possible safety hazards for vented emissions. There are many opportunities throughout the natural gas production and supply chain for gas to be released from containment and lost, such as pneumatic component venting, maintenance blowdowns, component failures, accidental release, and the like. Natural gas production and distribution infrastructure are spatially distributed. Efficient, wide area survey methods are needed to identify, localize, and quantify natural gas releases throughout these spatially distributed systems.

The disclosed unmanned aerial system (UAS) measures trace-gas concentration along the chosen UAV flight path at high frequency to detect anomalies associated with natural gas releases. Data from the UAV may be reconciled with atmospheric conditions to identify and quantify the mass flow rate of natural gas sources within an inspection area.

UAS Emissions Measurement System and Method

The disclosed method for emission rate quantification is based on an engineering control volume model. The UAS has a fast response, in situ trace-gas sensor payload and flies downwind of potential emission sources on transects that are nearly perpendicular to the average wind direction approximately +/−90 degrees. The trace-gas may include methane in some embodiments. The disclosed trace-gas sensor may be capable of measuring multiple hydrocarbon species typically found in natural gas and can be used to determine whether a gas leak consists of natural gas, i.e., methane and ethane are detected simultaneously, or only methane, thereby attributing whether the source of the leak is natural gas infrastructure, or anaerobic digestion or enteric fermentation. The disclosed sensors measure the crosswind and vertical profile of trace-gas concentration and maps out the spatial profile of trace-gas emissions from upwind sources as well as the characteristics of the background concentration variability.

FIG. 1A depicts an illustration of an unmanned aerial system (UAS) emissions measurement process and flight path 100, according to one embodiment. A representative flight path 102 of an unmanned aerial vehicle (UAV) 104 is downwind of a point source 108. In this example, the point source 108 is a pump jack, but the point source 108 may be any equipment having a potential to emit gas. The UAV 104 measures a cross-section of an emissions plume 106 from the point source 108 on a vertical plane. In addition to concentration, emission rate estimates are determined by wind velocity along the UAV flight path 102.

To capture a downwind "control surface" for the emissions estimate, the disclosed UAV 104 flies a raster grid pattern flight path 102 along a vertical plane that is perpendicular to a ground surface 110 and the average wind direction+/−90 degrees. The position of the UAV 104 and corresponding natural gas concentration measurement are recorded, such as by a global positioning system (GPS) position. The altitude of the UAV 104 relative to the ground 110 may be further quantified using a range-finding LIDAR, Sonar, radar, GPS altitude, and/or barometric pressure sensor.

Figure 1B:
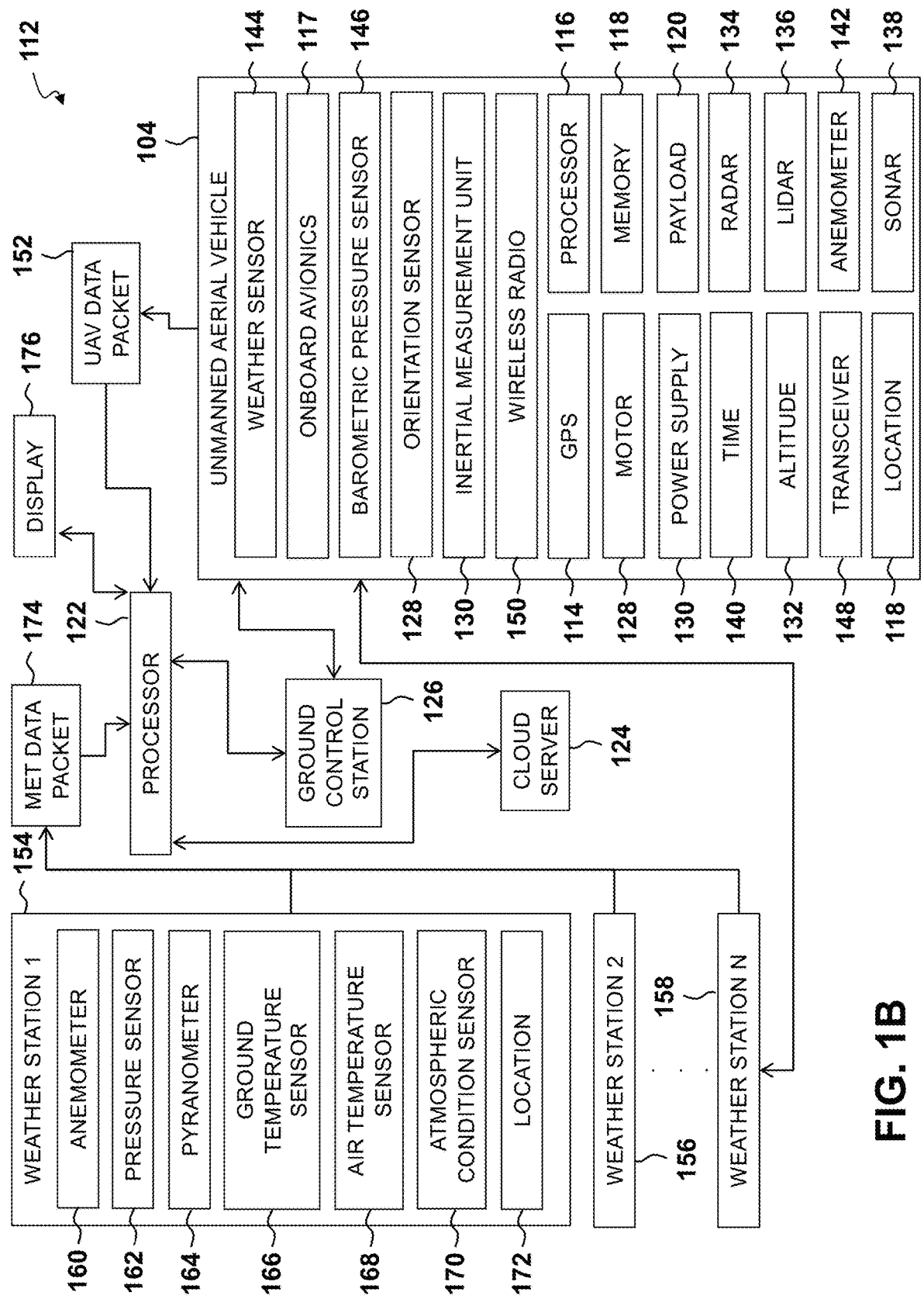
FIG. 1B depicts a high-level block diagram of a UAS emissions measurement system, according to one embodiment.

FIG. 1B depicts a high-level block diagram of a UAS emissions measurement system 112, according to one embodiment. The system 112 may include a UAV 104. In some embodiments, the UAV 104 may be a quadcopter-style aerial vehicle capable of hovering and flying the raster pattern flight path, as shown in FIG. 1A. In other embodiments, the UAV 104 may be a winged aerial vehicle. The UAV 104 may have any number of rotors, motors 128, wings, or the like to sustain flight and fly the determined UAV flight path. The UAV 104 may have the ability to fly in a three-dimensional flight path in the vicinity of a potential trace-gas source (108, FIG. 1A). The UAV 104 may fly ≤200 m from a 0.1 SCFH emissions point.

Embodiments of the unmanned aerial vehicle 104 may include any number of sensors shown in FIG. 1B based on the desired data. Embodiments of the weather station 154 may include any number of sensors shown in FIG. 1B based on the desired data. In some embodiments, the weather station 154 may only include an anemometer 160. In other embodiments, the weather station 154 may be integrated into the unmanned aerial vehicle 104. For example, the anemometer 160 may be integrated on the unmanned aerial vehicle 104. In another embodiment, the weather station 154 may be located on another aerial vehicle or unmanned aerial vehicle. For example, the system may include two or more unmanned aerial vehicles where at least one unmanned aerial vehicle is recording trace-gas gas concentrations and at least one unmanned aerial vehicle is recording meteorological data. The weather station 154 may be stationary or mobile. The weather station 154 may be in relatively close proximity to the unmanned aerial vehicle 104. In some embodiments, the weather station 154 may record meteorological data. In some embodiments, the weather station 154 may be from a third-party source, such as a third-party sensor. In some embodiments, the weather station 154 may predict future meteorological measurements. The nearest temporal Meteorological (MET) data packet 174 may be combined with the UAV data packet or trace-gas data packet 152. The frequency of each of the MET data packet 174 and the trace-gas data packet 152 may be different but close in some embodiments. The frequency of each of the MET data packet 174 and the trace-gas data packet 152 may be substantially the same in some embodiments.

The UAV 104 may have a global positioning system 114, an onboard avionics 117, and/or a location sensor 118 to track a spatial position of the UAV 104 as it travels along the flight path (102, FIG. 1A). The UAV 104 may track its spatial position as it measures gas concentrations along the flight path such that each gas measurement of the UAV 104 corresponds to a spatial position where that gas measurement was taken. The global positioning system 114, onboard avionics 117, and/or location sensor 118 may be in communication with a UAV processor 116 having addressable memory 118. In some embodiments, the location of the UAV 104 may be determined by the onboard avionics 117. The onboard avionics 117 may include a triangulation system, a beacon, a spatial coordinate system, or the like. The onboard avionics 117 may be used with the GPS 114 and/or location sensor 118 in some embodiments. In other embodiments, the UAV 104 may use only one of the GPS 114, the onboard avionics 117, and/or the location sensor 118.

The UAV 104 may include a payload 120 in communication with the UAV processor 116. The payload 120 may include one or more gas concentration sensors. The payload 120 may be detachably attached to the UAV 104. In other embodiments, the payload 120 may be fixedly attached to the UAV 104. The payload 120 may be in communication with the UAV processor 116. In one embodiment, the payload 120 may be an ultra-lightweight, low power, Part per Billion (ppb) sensitivity, mid-Infrared ($\lambda$=3-8 µm), open path trace-gas concentration sensor with sampling rate >0.1 Hz.

The UAV processor 116 may also be in communication with an orientation sensor 128, an inertial measurement unit (IMU) 130, an altitude sensor 132, a radar 134, a LIDAR 136, and/or a Sonar 138 for generating additional information on the spatial position of the UAV 104 during each gas measurement by the payload 120. The orientation sensor 128 may be used to determine an orientation of the UAV 104 relative to ground. In some embodiments, the orientation sensor 128 may be a compass. The IMU 130 may be used to determine attitude, velocity and/or position of the UAV 104. The altitude sensor 132 may be used to determine an altitude of the UAV 104. The LIDAR 136, Sonar 138, and/or radar 134 may be used to determine a relative altitude of the UAV 104.

In some embodiments, the UAV processor 116 may also be in communication with an anemometer 142, one or more weather sensors 144, and/or a barometric pressure sensor 146. The anemometer 142 may be used to measure the speed of the wind. The anemometer 142 may be attached to the UAV 104 at a point so as to ensure an accurate wind measurement without interfering with the propulsion from the motors 128 or sensors of the payload 120. The weather sensor 144 may measure weather and/or atmospheric conditions. The barometric pressure sensor 146 may measure a barometric pressure. The anemometer 142, weather sensor 144, and/or barometric pressure sensor 146 may be used to record data at each gas measurement from the payload 120.

In some embodiments, the UAV processor 116 may also be in communication with a time measurement device 140. The time measurement device 140 may be used to record the time for each gas measurement measured by the payload 120 of the UAV 104. Each gas measurement, position measurement, orientation measurement, weather measurement, and/or relative altitude measurement may be 'time-stamped' so as to be combined by the processor 122 and/or the UAV processor 116.

The UAV processor 116 may also be in communication with a transceiver 148 and/or a wireless radio 150. The wireless radio may include LTE, satellite, or the like. The transceiver 148 and/or wireless radio 150 may be used to communicate between the UAV 104 and the processor 122, the ground control station (GCS) 126, and/or a cloud server 124.

The processor 122, the cloud server 124, the ground control station (GCS) 126, and/or the UAV processor 116 may determine a flight path for the UAV 104 having the payload 120. In some embodiments, the flight path may be determined on a site-specific basis. In other embodiments, the flight path may be determined and/or flown via a user of the GCS 126. In other embodiments, the flight path may be self-determined, autonomous control. The flight path is used to measure gas concentration along a crosswind transect, and vertical profile, in the vicinity of a possible gas emissions point. This flight plane of the flight path is designed to capture the atmospheric trace-gas background as well as emissions signature, i.e., elevated ambient concentration, from all potential sources at an inspection site.

The UAV 104 may have the UAV processor 116 in communication with addressable memory 118, a GPS 114, one or more motors 128, and a power supply 130. The UAV 104 may communicate gathered payload 120 data to the UAV processor 116. The power supply 130 may be a battery in some embodiments. In some embodiments, the processor 122 may be a part of the UAV 104, the cloud server 124, the GCS 126 used to control the UAV 104, or the like.

The UAV processor 116 may receive gas data from the one or more gas sensors of the payload 120. The UAV processor 116 may also receive spatial position data from the GPS 114, altitude sensor 132, location sensor 118, radar 134, LIDAR 136, Sonar 138, orientation sensor 128, IMU 130, and/or onboard avionics 117. In some embodiments, the UAV processor 116 may also receive weather data from the weather sensor 144, the barometric pressure sensor 146, and/or the anemometer. The UAV processor 116 may also receive the time from the time measurement device 140. The UAV processor 116 may fuse the gas data from the payload 120 with the UAV 104 spatial position data, weather data, and/or time to form a trace-gas Data Packet 152.

The trace-gas data packet 152 may be sent to the processor 122, ground control station 126, and/or cloud server 124 via the transceiver 148 and/or wireless radio 150. In some embodiments, the wireless radio 150 or cellular connection may be used for remote data transfer between the UAV 104, the GCS 126, the processor 122, and/or the cloud server 124. The wireless interface or cellular connection between the UAV 104, the GCS 126, the processor 122, and/or the cloud server 124 may be used to performing advanced data analysis functions. Direct, bidirectional data transfer may occur between the UAV 104 and the GCS 126, between the UAV 104 and the cloud server 124, and/or between the GCS 124 and the cloud server 124.

The processor 122 may be a part of the UAV 104, the GCS 126, the cloud server 124, and/or the weather station 154 in some embodiments. While multiple sensors and devices are depicted for the UAV 104, any number of sensors and/or devices may be used based on the system 112, desired accuracy, time limitations, weight limitations, and the like.

One or more weather stations 154, 156, 158 may provide local weather information to the UAV 104, payload 120, GCS 126, and/or cloud server 124. The weather stations 154, 156, 158 may also receive information from the UAV 104, payload 120, GCS 126, and/or cloud server 124.

The first weather station 154 may include one or more anemometers 160, one or more pressure sensors 162, one or more pyranometers 164, one or more ground temperature sensors 166, one or more air temperature sensors 168, one or more atmospheric condition sensors 170, and one or more location sensors 172. The anemometer may be used to measure wind speed. The pressure sensor 162 may measure a pressure. The pyranometer may be used to measure solar irradiance. The ground temperature sensor 166 may be used to measure a temperature of the ground. The air temperature sensor 168 may be used to measure a temperature of the air. An atmospheric condition sensor 170 may be used to measure data relating to the atmosphere. The location sensor 172 may be used to measure the location of the weather station 154. Each weather station 154, 156, 158 may include any number of sensors and/or devices based on the system 112, desired accuracy, number of weather stations over a geographical area, and the like.

In some embodiments, sensors and/or devices of the weather station 154 may be located and/or duplicated on the UAV 104. High resolution (<0.1 m/s), high-frequency measurements (>5 Hz) of wind speed and direction may be recorded using one or more wind sensors, and one or more additional weather/micro-meteorological sensors including, air temperature, humidity, atmospheric pressure, solar irradiance, ground surface temperature—from the ground via a weather station 154, 156, 158 and/or from the UAV 104 as disclosed herein. For example, both the weather station 154 and the UAV 104 may include respective anemometers 160, 142, which may be used to generate wind speed data. The weather station data may be associated with a time the data was collected and/or generated. The weather station data may be used to generate a Meteorological (MET) data packet 174. The Meteorological data packet 174 may be sent to the processor 122, ground control station 126, cloud server 124, and/or UAV 104. The Meteorological data packet 174 may include measurements and/or predictions of the atmosphere, weather, temperature, wind patterns, or the like.

Each trace-gas Data Packet 152 may be combined with the nearest temporal Meteorological Data Packet 174 by the processor 122 and saved on the GCS 126 and/or cloud server 124. The data may be uploaded to the cloud server 124 in real-time, near real-time, or at a later time. The combined trace-gas data packet 152 and Meteorological data packet 174 may be used to determine a trace-gas emission rate of the trace-gas source by the processor 122, GCS 126, and/or cloud server 124. The trace-gas emission rate may be determined based on a control volume model that combines concentration measurements from the UAV flight plane with measured wind speed, direction and spatial gradient to determine the mass flow rate emissions from sources in the inspection area.

This determined trace-gas emission rate may be stored by the processor 122, GCS 126, and/or cloud server 124. In some embodiments, the determined emission rate may be shown on a display 176. The display 176 may show source emissions data on a map, satellite image, aerial image, two-dimensional color map, two-dimensional contour map, and/or three-dimensional topographical surface/mesh.

Figure 1C:
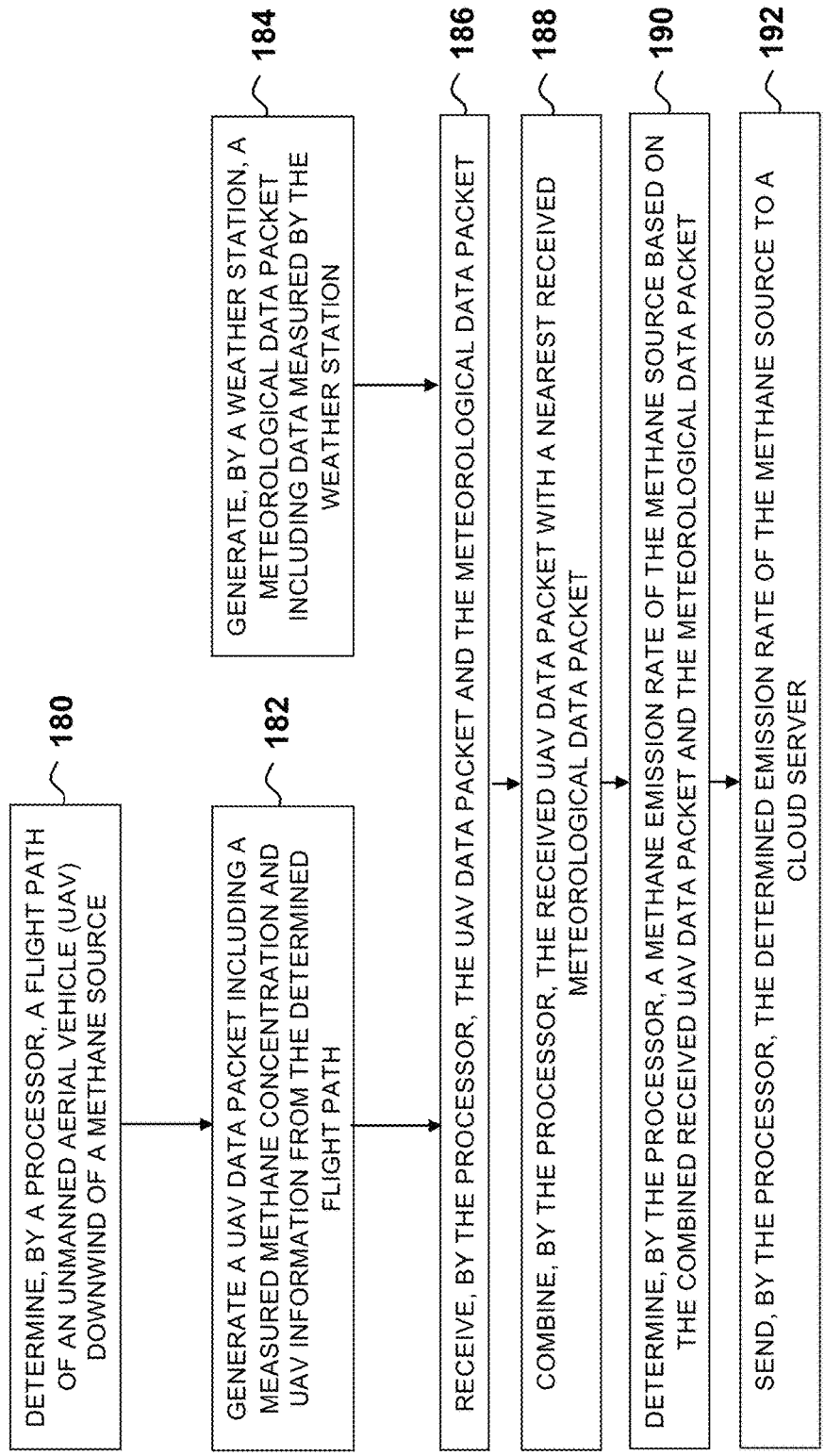
FIG. 1C depicts a high-level flowchart of a method embodiment of determining emissions measurements via unmanned aerial vehicle (UAV) data and weather data, according to one embodiment.

FIG. 1C depicts a high-level flowchart of a method 178 embodiment of determining emissions measurements via unmanned aerial vehicle (UAV) data and weather data, according to one embodiment. The method 178 may include determining, by a processor, a flight path of a UAV downwind of a trace-gas source (step 180). The method 178 may then include generating a UAV data packet include a measured trace-gas concentration and UAV information from the determined flight path (step 182). The method 178 may then include generating, by a weather station, a Meteorological data packet including data measured by the weather station 184. The method 178 may then include receiving, by the processor, the UAV data packet and the Meteorological data packet (step 186). The method may then include combining, by the processor, the received UAV data packet with a nearest temporal, i.e., in time, received Meteorological data packet (step 188). The method 178 may then include determining, by the processor, a trace-gas emission rate of the trace-gas source based on the combined received UAV data packet and the Meteorological data packet (step 190). The method 178 may then include sending, by the processor, the determined emission rate of the trace-gas source to a cloud server (step 192).

Data Transfer Scheme

Figure 2:
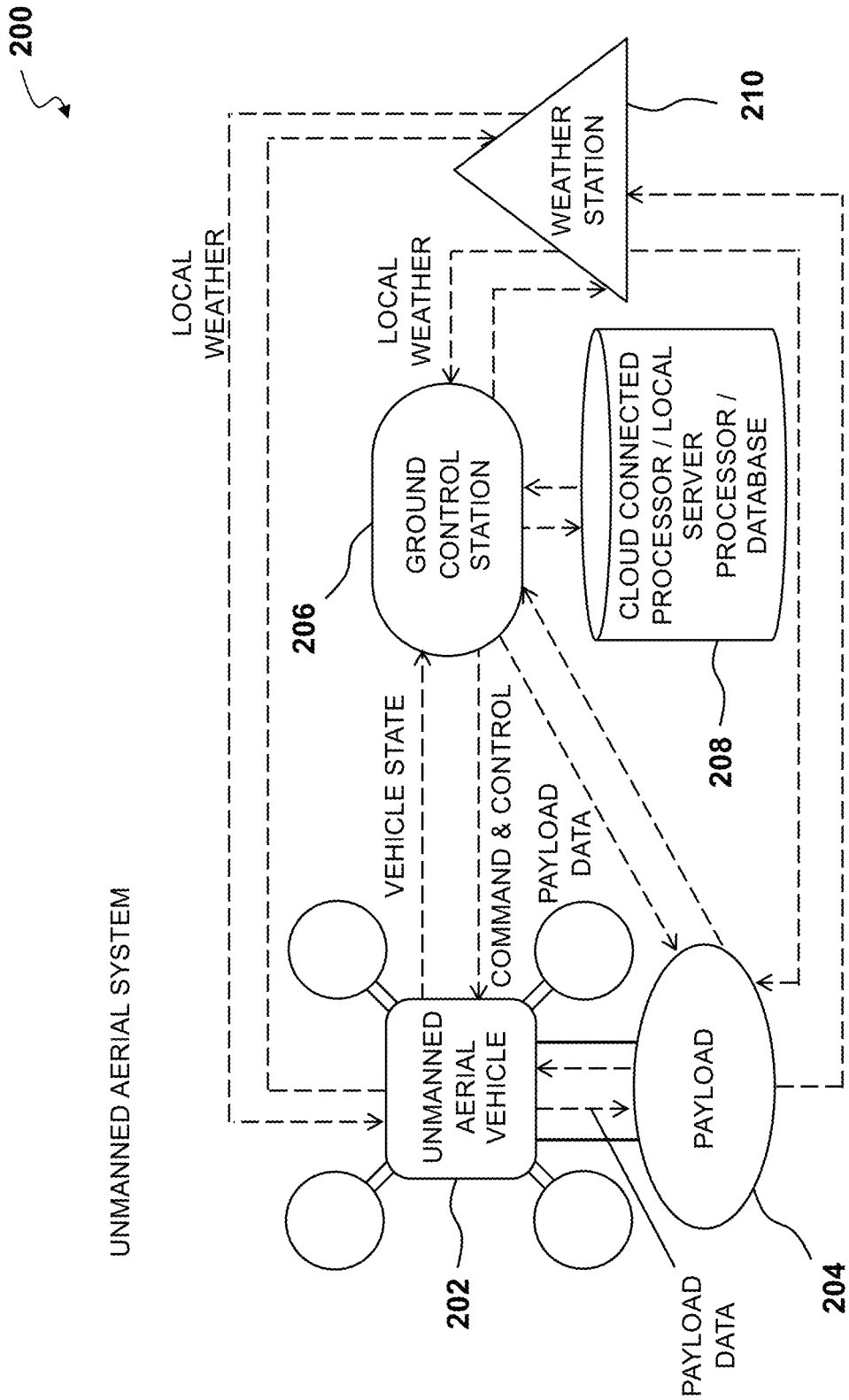
FIG. 2 depicts a data flow in a single sensor and unmanned aerial vehicle (UAV) configuration with a Ground Control Station (GCS) as a point of interface between the UAS and the cloud-connected Processor, Local Server Processor, and/or Database, according to one embodiment.

FIG. 2 depicts a data flow 200 in a single sensor and unmanned aerial vehicle (UAV) 202 configuration with a ground control station (GCS) 206 as a point of interface between the UAV 202 and the cloud-connected processor, local server processor, and/or database 208, according to one embodiment. The general flow of data is from one or more gas concentration sensors, i.e., payload 204, affixed to one or more UAVs 202 and wirelessly transmitted to the centralized GCS 206 and then transferred to the cloud-connected Server, Processer, Local Server Processor, and/or Database 206.

A weather station 210 may provide local weather information to the UAV 202, payload 204, and/or GCS 206. The weather station 210 may also receive information from the UAV 202, GCS 206, and/or payload 204. The UAV 202 vehicle state and other information may be transmitted by the UAV 202 and received by the GCS 206. The GCS may send command and control information to the UAV 202. The payload 204 may provide and/or receive payload data between the payload 204 and the UAV 202 and/or the GCS 206.

Figure 3:
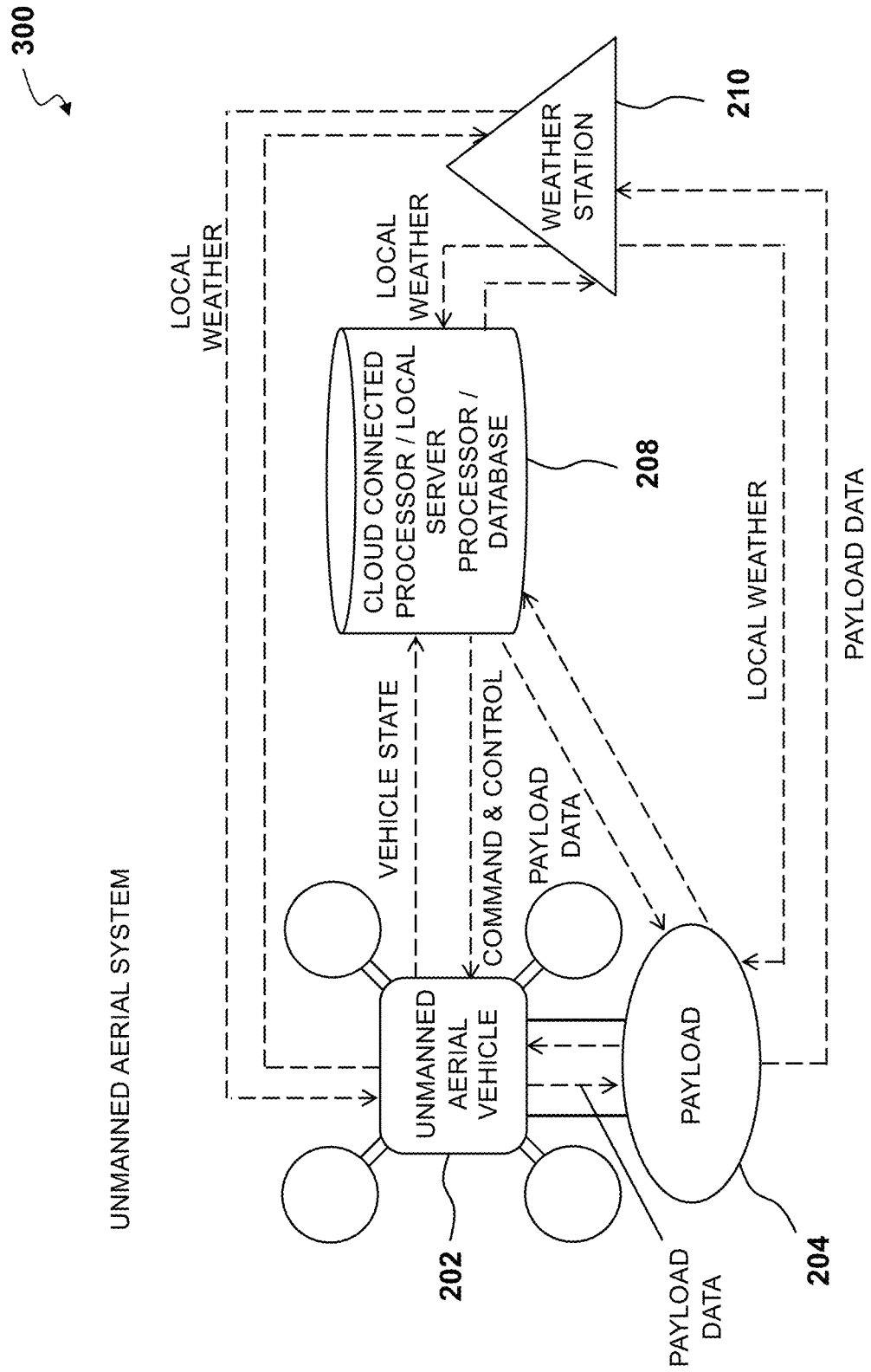
FIG. 3 depicts a data flow in a single sensor and UAV configuration with the UAS directly interfacing with the cloud-connected Processor, Local Server Processor, and/or Database, according to one embodiment.

FIG. 3 depicts a data flow 300 in a single sensor and UAV 202 configuration with the UAV 202 directly interfacing with the cloud-connected processor, local server processor, and/or database 208, according to one embodiment. In another embodiment, the payload(s) 204, UAV(s) 202, and/or weather station(s) 210 communicate directly with a cloud server processor, local server processor, and/or database 208. In all cases, each subsystem, i.e., UAV 202; payload 204; GCS (see FIG. 2); cloud server processor, local server processor, and/or database 208; and weather station 210, may or may not have the ability to directly communicate with each other subsystem, as shown in FIGS. 1A-2. At the GCS (see FIG. 2), and/or cloud server processor, local server processor, and/or database 208, the data from the payload 204 is coupled with local weather station 210 data through local private networks and/or publicly available over the Internet. The data can then be post-processed on the GCS (see FIG. 2), on a local server, and/or on a cloud-hosted server 208.

Figure 4:
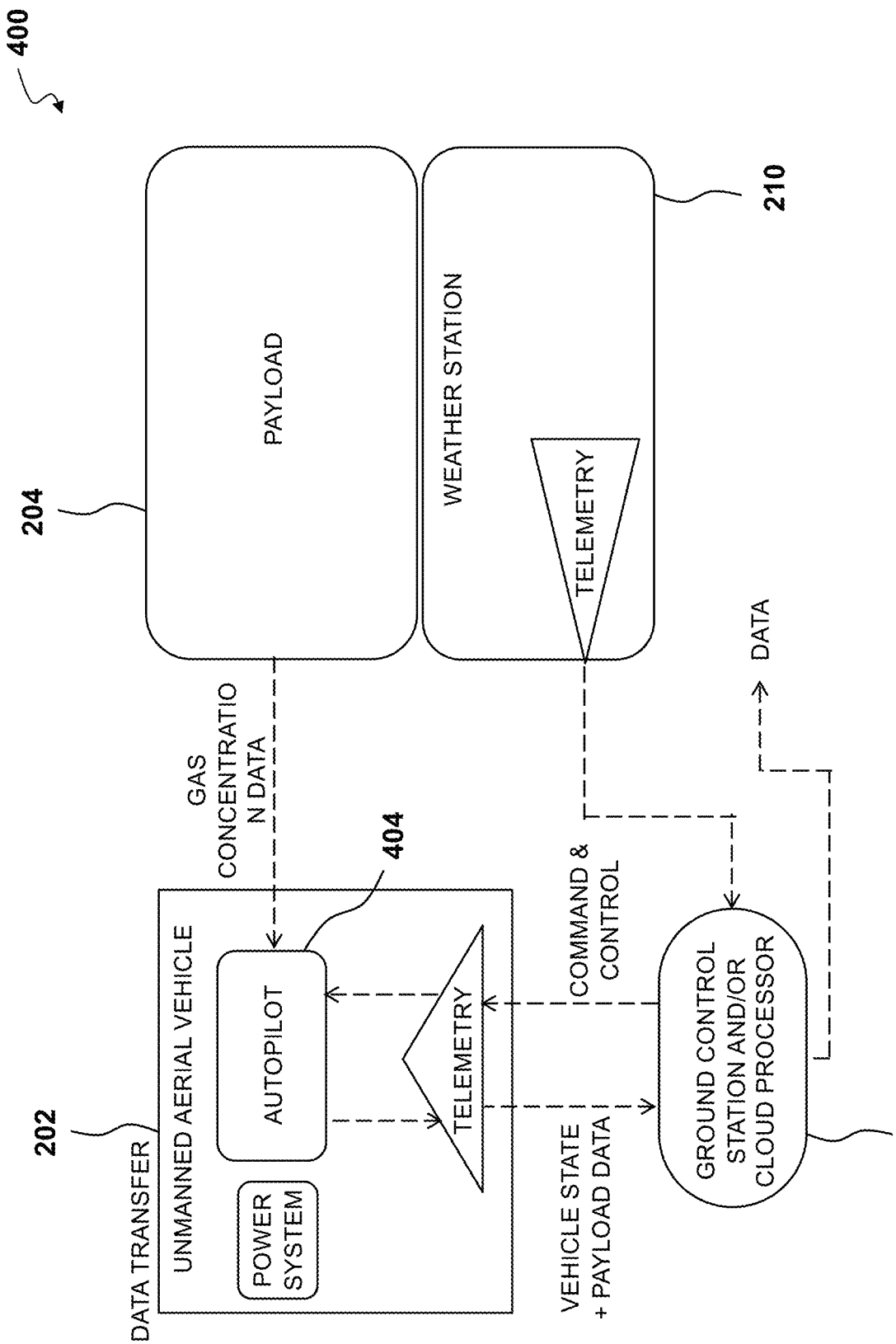
FIG. 4 depicts a detailed data transfer from a single sensor with a single UAV, where this combination of devices comprise a UAS, according to one embodiment.

FIG. 4 depicts a detailed data transfer 400 from a single sensor with a single UAV 202, where this combination of devices comprise a UAS, according to one embodiment. Data from the payload 204 transfers to the UAV 202 and directly to an autopilot 404 via a serial connection. In some embodiments, the data transfer from the UAV 202 to the autopilot 404 may be any connection hardwire or wireless. Then, the data transfer is fused with GPS location and time, barometric pressure, altitude, relative altitude from LiDAR, Sonar, Radar, and/or UAV orientation, which forms a UAV Data Packet. The UAV Data Packet may be transferred to the GCS and/or cloud processor 402 via a 500 mW 915 MHz Frequency Hopping Spread Spectrum (FHSS) transceiver. In some embodiments, the UAV Data Packet may be transferred via any wireless radio. In parallel, a weather station 210 having at least an anemometer, and may contain one or more pressure sensors, pyranometers, i.e., for solar irradiance, ground temperature sensors, air temperature sensors, and/or any sensor necessary for quantifying current atmospheric conditions, may form a Meteorological Data Packet. The GCS and/or cloud processor 402 receives both the Meteorological Data Packet and UAV Data Packet at a frequency greater than 0.1 Hz. Each UAV Data Packet is fused with the nearest temporal Meteorological Data Packet and saved on the GCS and/or a cloud server, local server, and/or database 402 in an ASCII, binary, or any file necessary. The data may be uploaded to a cloud server in real-time, near real-time, or at a later time.

Background Calculation

Figure 5:
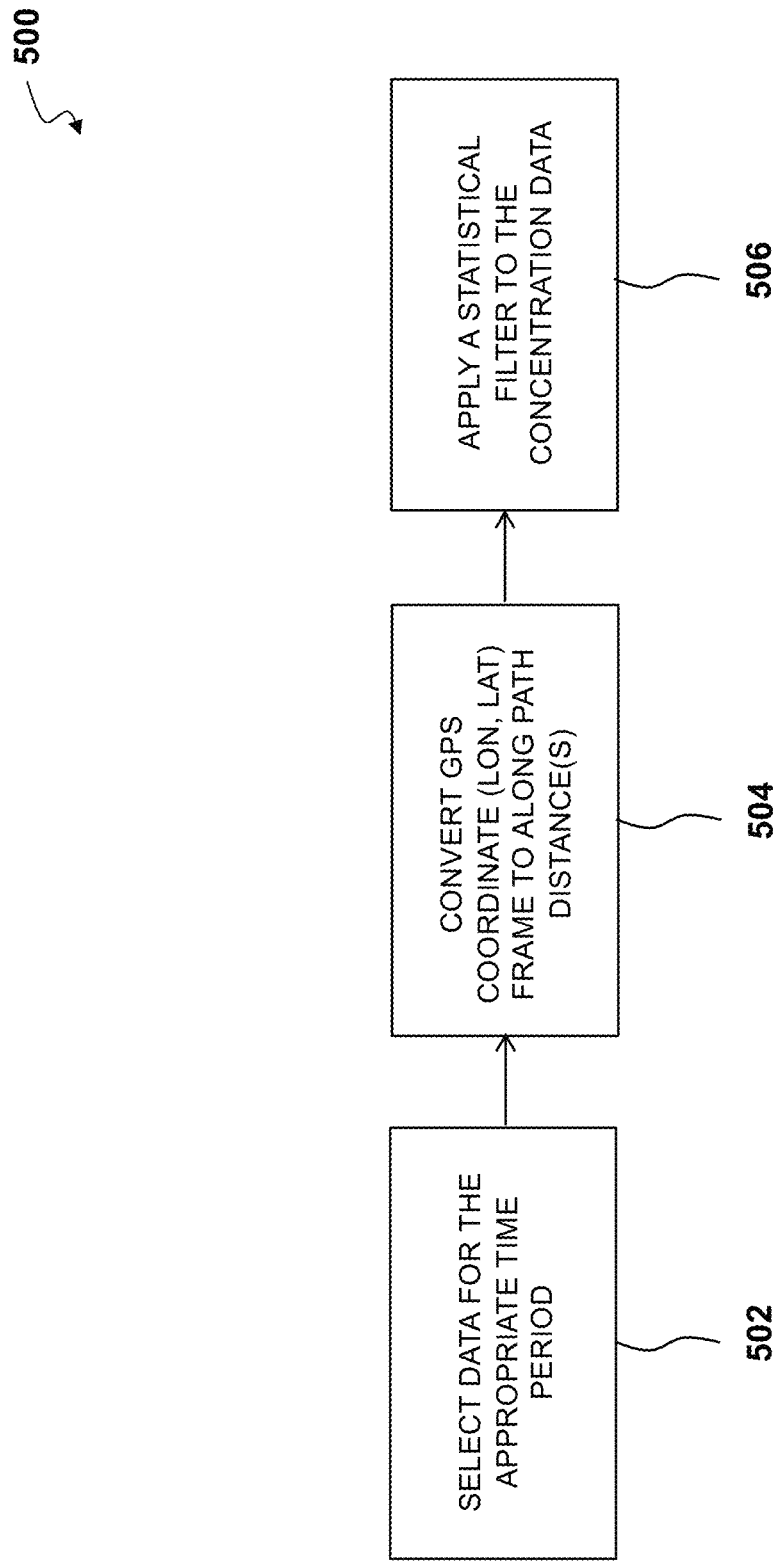
FIG. 5 depicts a background gas concentration workflow, according to one embodiment.

FIG. 5 depicts a background gas concentration workflow 500, according to one embodiment. The first step in the emissions estimate model is to calculate the control volume in-flow condition. The in-flow condition will determine total emissions for the source area that is of interested, by accounting for and subtracting any emissions from upwind sources. Typically, it is assumed that the background concentration measured on the upwind side of the source inspection area is a good representation of the local background concentration and provides an estimate of the upwind in-flow condition. The procedure for calculating the background concentration starts with selecting data for the appropriate time period (step 502). Then, the GPS coordinates, i.e., longitude and latitude, are framed to along a path distance (step 504). Third, a statistical filter is applied to the concentration data (step 506).

Figure 6:
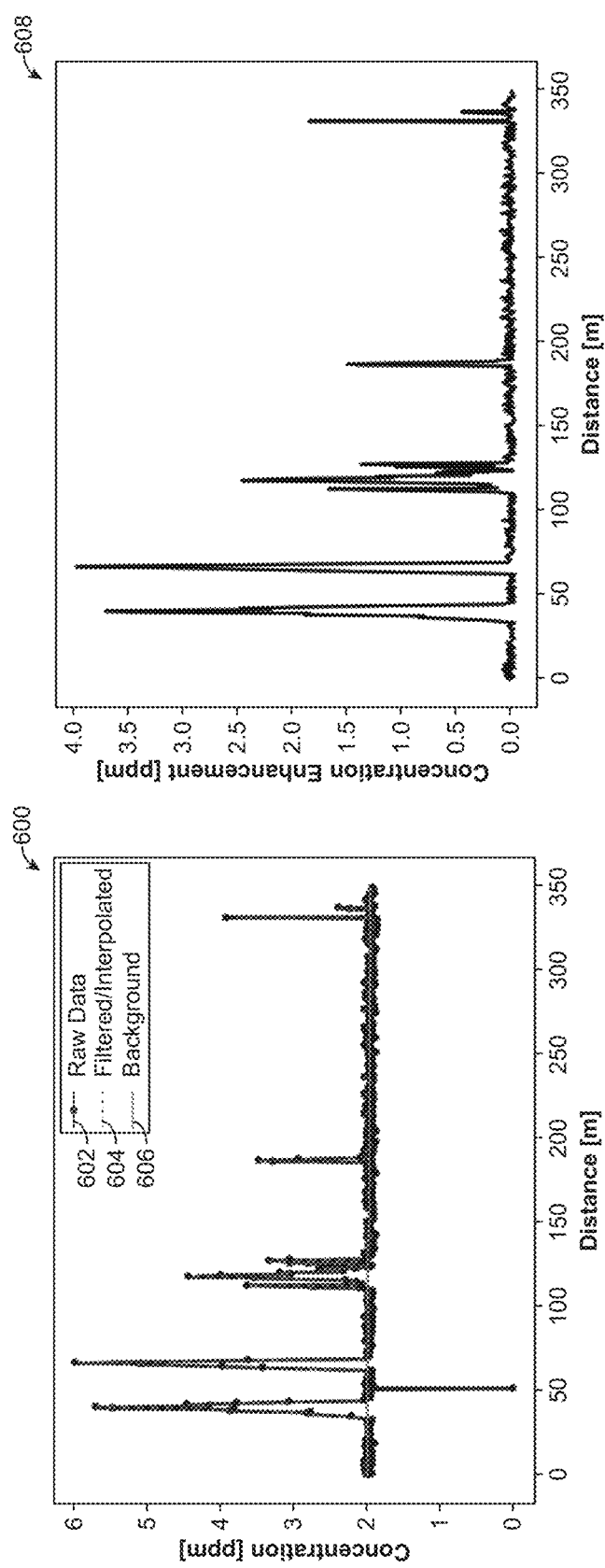
FIG. 6A depicts a graph showing raw concentration data, filtered/interpolated data, and a background concentration estimation, according to one embodiment.
FIG. 6B depicts a graph showing a concentration enhancement data resolved utilizing a sliding window median filter, according to one embodiment.

FIG. 6A depicts a graph 600 showing raw concentration data 602, filtered/interpolated data 604, and a background concentration estimation 606, according to one embodiment. FIG. 6B depicts a graph 608 showing a concentration enhancement data resolved utilizing a sliding window median filter, according to one embodiment. In additional embodiments, a low-pass filter can be applied to the concentration series to generate a background concentration series. In additional embodiments, such as a flight path that circumnavigates the emission source, the background concentration can be calculated by calculating the mass-flow weighted average of the detected concentration upwind of the potential emission source. In embodiments where a filtering function is used, raw concentration data as a function of distance, i.e., spatial coordinate, is filtered using the prescribed filter. The filter window scale is determined based on a typical, or expected, gas plume width. For example, if the maximum plume width is expected to be on the order of 10 m, the filter scale would be set to three to five times the max plume width. The median filter also removes infrequent transients, or dropouts, in the concentration measurement caused by communication interference, or platform vibrations. The background concentration is subtracted from the total concentration to obtain the concentration enhancement. The concentration enhancement signal represents the signature of an upwind emission source where the flight path is only downwind of the emission source. In embodiments where the flight path circumnavigates the emission source, the concentration enhancement signal represents the signature of an emission within the bounds of the flightpath. The signature calculated is used to quantify the emissions released by the local source.

Spike/Emissions Detection

Spike detection on the concentration enhancement signal is performed as part of the emissions calculation to determine if an emission source is present upwind of the flight path. This is a binary determination step, after performing spike detection on the concentration enhancement signal the remaining portion of the emissions algorithm only continues if an upwind emission source is present.

A statistical filter is then applied to the concentration enhancement signal to identify "spikes" in the data that indicate trace-gas plumes from nearby sources. The statistical filter is determined by analysis of the Cumulative Distribution Function (CDF) for the concentration enhancement, and targets extremum data points based on a prescribed percentile threshold. In additional embodiments, the spike is detected with a quantile analysis. In additional embodiments, the spike is detected with a high-pass filter and threshold. The selected points are then analyzed for contiguity and consolidated to form spatially continuous events. Each spike event may be further analyzed according to other metrics such as spatial extent, amplitude, magnitude, variance, and waveform shape. Individual spike events may be included or excluded through a selection process based on these derived quantities.

Plane Projection

Figure 7:
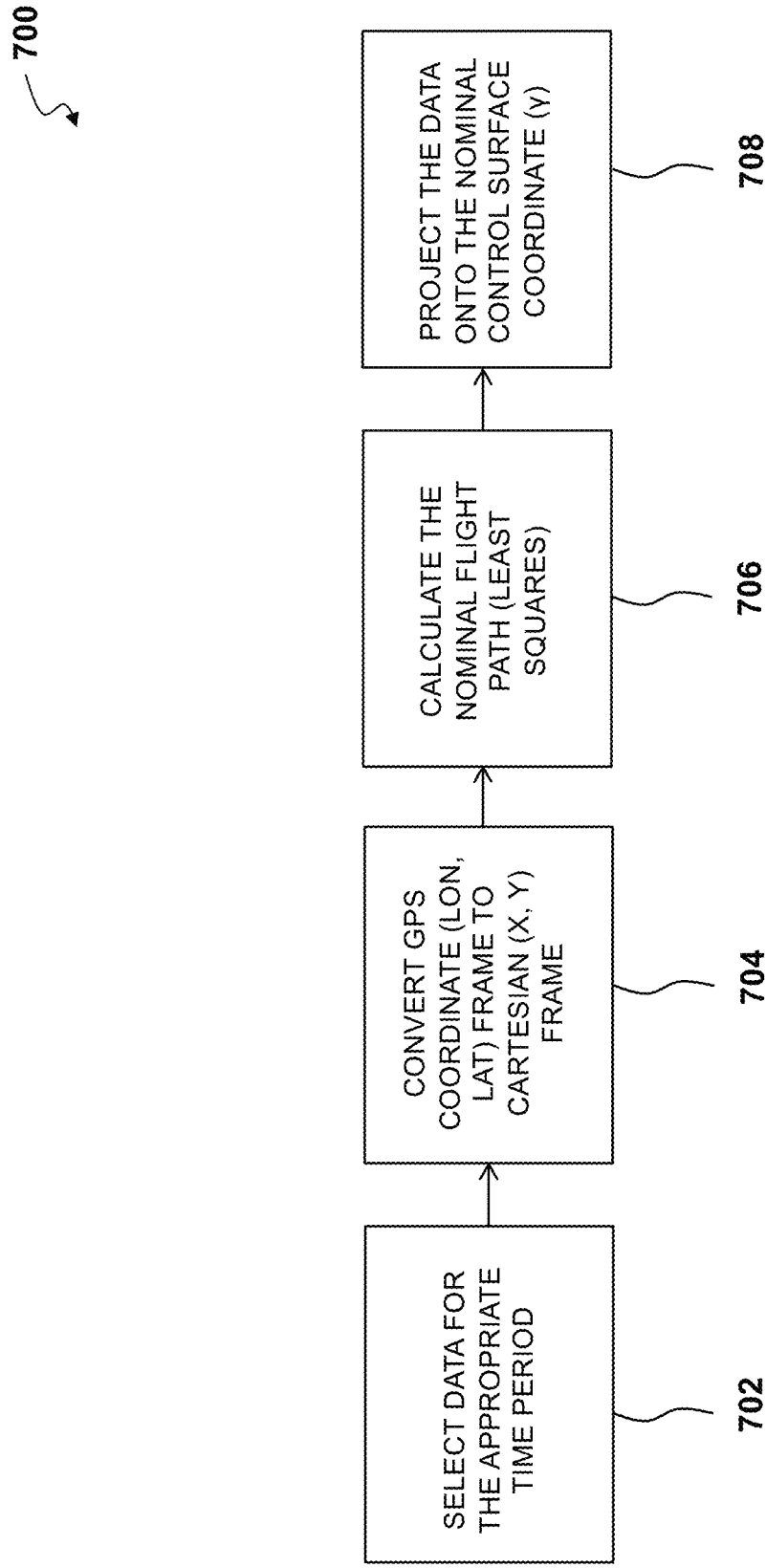
FIG. 7 depicts a plane projection workflow, according to one embodiment.

FIG. 7 depicts a plane projection workflow 700, according to one embodiment. Due to variability in the flight trajectory caused by wind and GPS uncertainty, it is not generally possible to fly perfect transects along the same line at various heights. Therefore, an automatic detection of the nominal flight path, or plane, orientation may be performed using a least-squares fitting method to the data. First, data is selected for the appropriate time period (step 702). Then, a GPS coordinate, i.e., longitude and latitude, frame is converted to a Cartesian frame, i.e., x and y (step 704). Then, the nominal flight path is calculated, e.g., least squares (step 706). Finally, the data is projected onto the nominal control surface coordinate, i.e., y (step 708).

Figure 8:
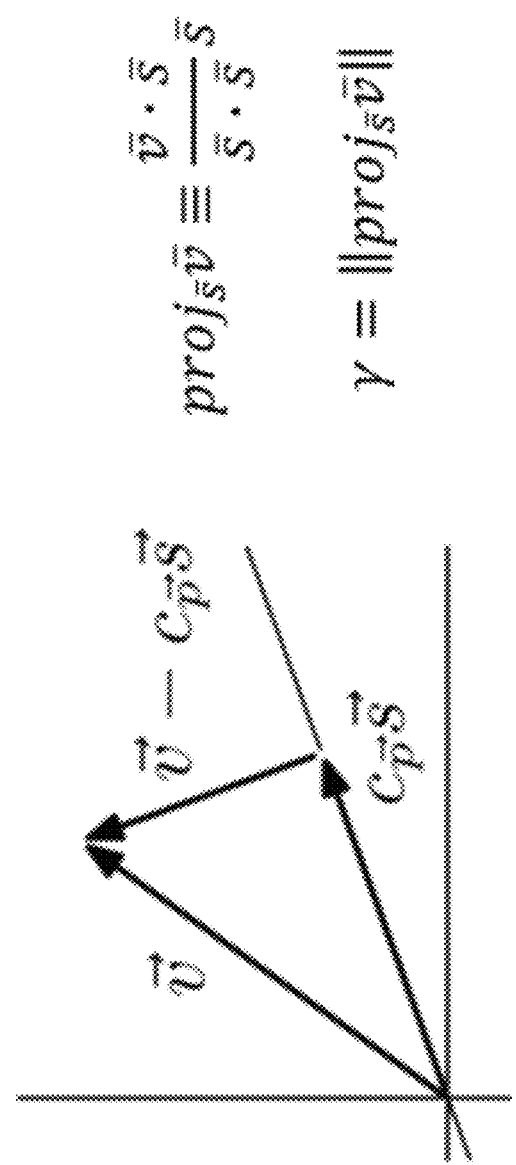
FIG. 8 depicts formulas for an orthogonal vector projection, according to one embodiment.

FIG. 8 depicts formulas 800 for an orthogonal vector projection, according to one embodiment. The projection is accomplished utilizing a linear algebra vector projection equation. Other projected vector formulas are possible and contemplated to determine the vector projection. Gamma ($\gamma$) is the vector norm, which is the length of the vector, as shown in FIG. 8.

Figures 9A, 9B:
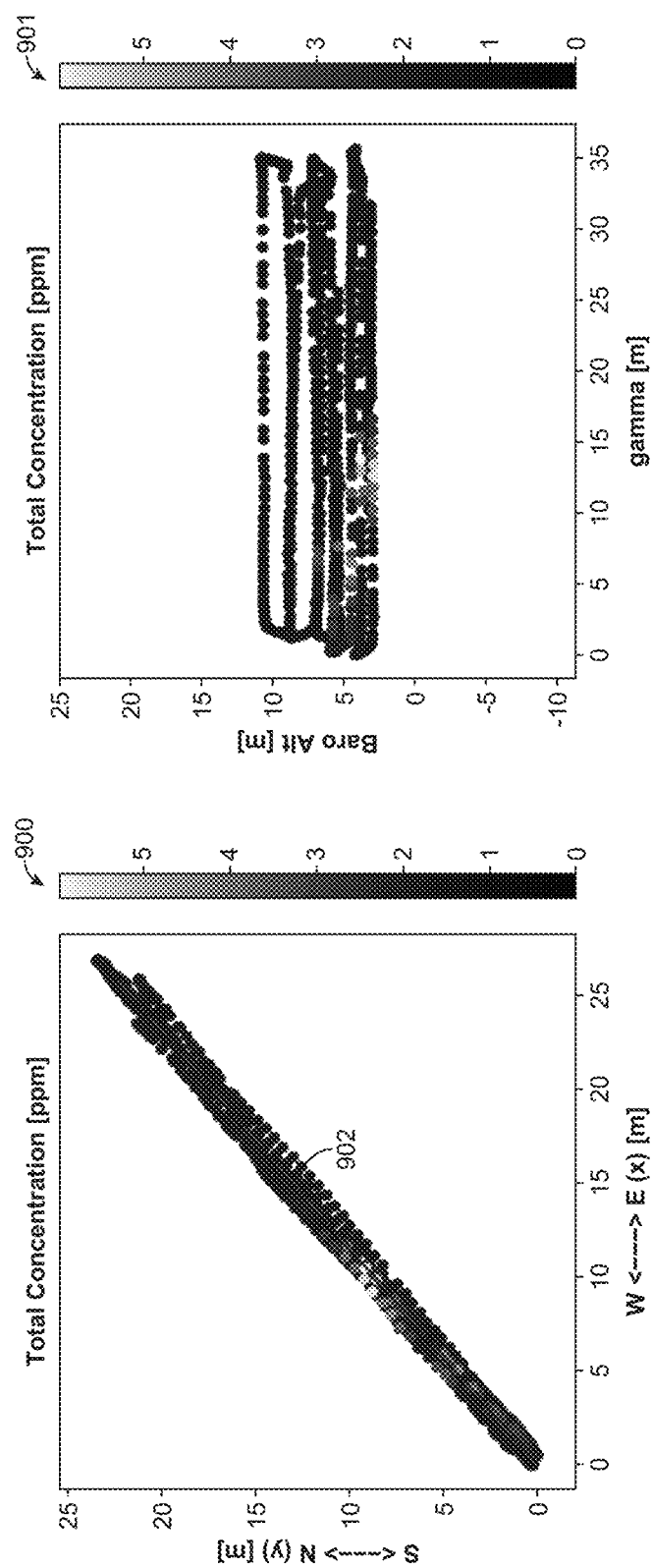
FIG. 9A depicts an overhead view of the flux plane flight trajectory with a derived regression line used for projection, according to one embodiment.
FIG. 9B depicts a flight trajectory projected onto the (y, z) plane, according to one embodiment.

FIG. 9A depicts a graph 900 of an overhead view of the flux plane flight trajectory with derived nominal flight plane trajectory used for projection, according to one embodiment. FIG. 9B depicts a graph 901 of a flight trajectory projected onto the (y, z) plane, according to one embodiment. The line 902 in the FIG. 9A represents the best estimate for the nominal flight plane trajectory, onto which the measurement coordinates are projected. FIG. 9B shows the vertical profile of concentration measurements as a function of the projected flight plane coordinate, i.e., gamma, and the altitude.

Interpolation

FIG. 10A depicts a graph 1000 of projected values along the (y, z) plane, according to one embodiment. FIG. 10B depicts a graph 1001 of an averaged and interpolated flux plane, according to one embodiment. Once the background concentration value is measured or estimated, the value is subtracted at each point along the flight path to obtain the concentration enhancement, and the measurements are averaged and interpolated on a continuous grid across the flight plane. A grid is created with a specified resolution over the range of coordinates in the projected flight plane. The concentration measurements within each grid cell are averaged, if no measurements exist for a particular grid cell then the value is left empty or replaced with null. After the grid is populated with the average measurements, a linear interpolation is applied to fill the grid with continuous concentration values. Some values on the grid have a negative concentration enhancement, this is important to ensure that the calculation returns a zero value for the flux when no upwind emission source is present.

Generation of a Control Surface

As an alternative method to projecting the measurements to a plane and interpolating the point concentrations onto a grid, a control surface can be directly calculated from the measurement points in three-dimensional space. This process involves calculating a horizontal value that represents the distance along the control surface. For planar or planar-like control surfaces, the value can be calculated as the incremental distance from one extent of the plane to the other extent of the plane. For flight paths that fully circumnavigate (FIG. 18A) or partially circumnavigate a source (FIG. 18B), the value can be calculated as the distance along the flight path from any specified starting point.

Figure 26:
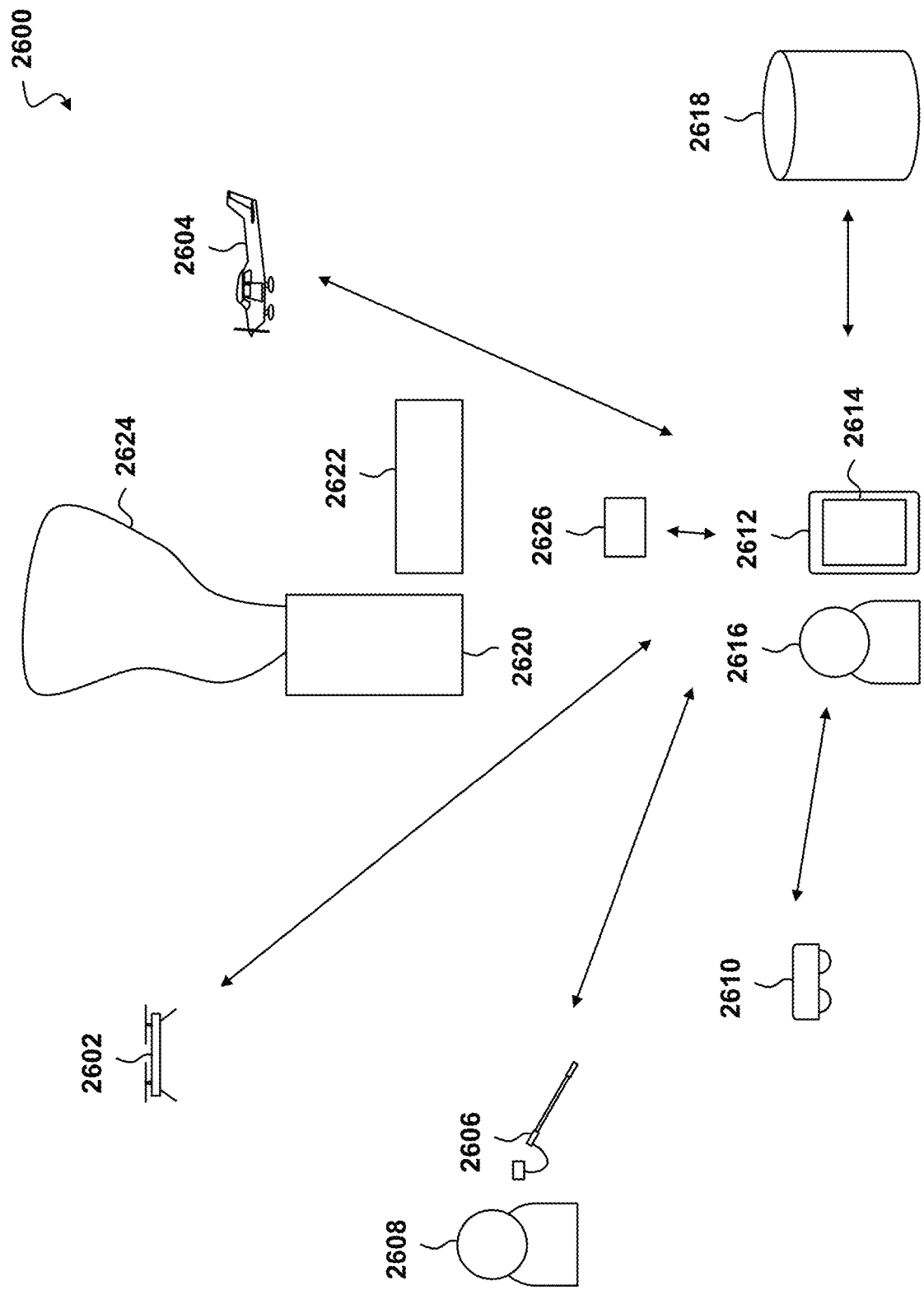
FIG. 26 depicts a system for detecting trace gasses, according to one embodiment.

The circumnavigated path can be generated by a series of flight lines shown in green (FIG. 19) that are a set distance from the equipment being inspected. The paths can be generated using a handheld GPS, map, drawing, or other geo-referenced source (FIG. 26). The partially circumnavigated path shown by the path 1904 can be calculated by the average wind direction 1908 and variance 1906, or by other methods.

Figure 20:
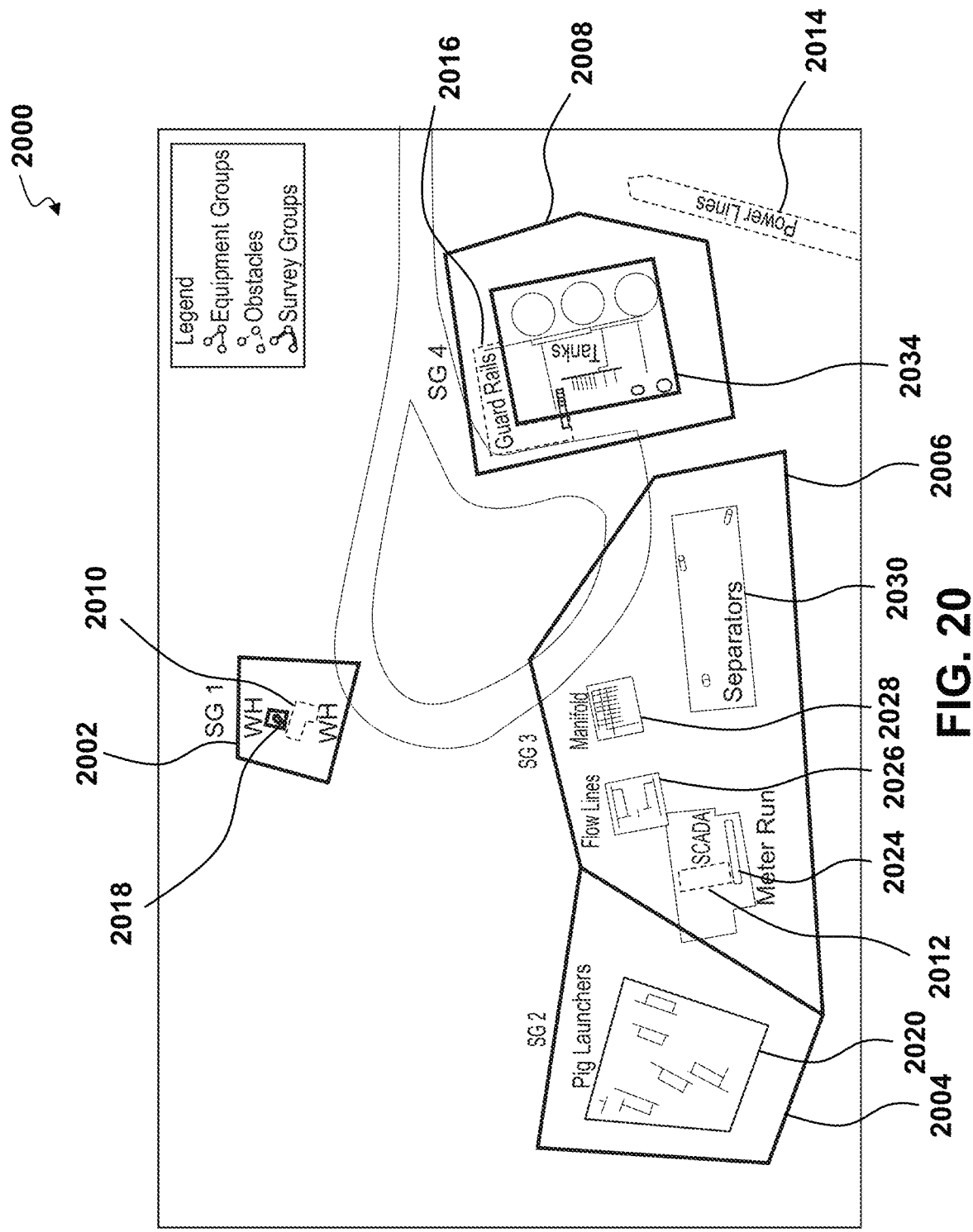
FIG. 20 depicts flight paths that may be created based upon equipment or equipment grouping, according to one embodiment.
Figure 21:
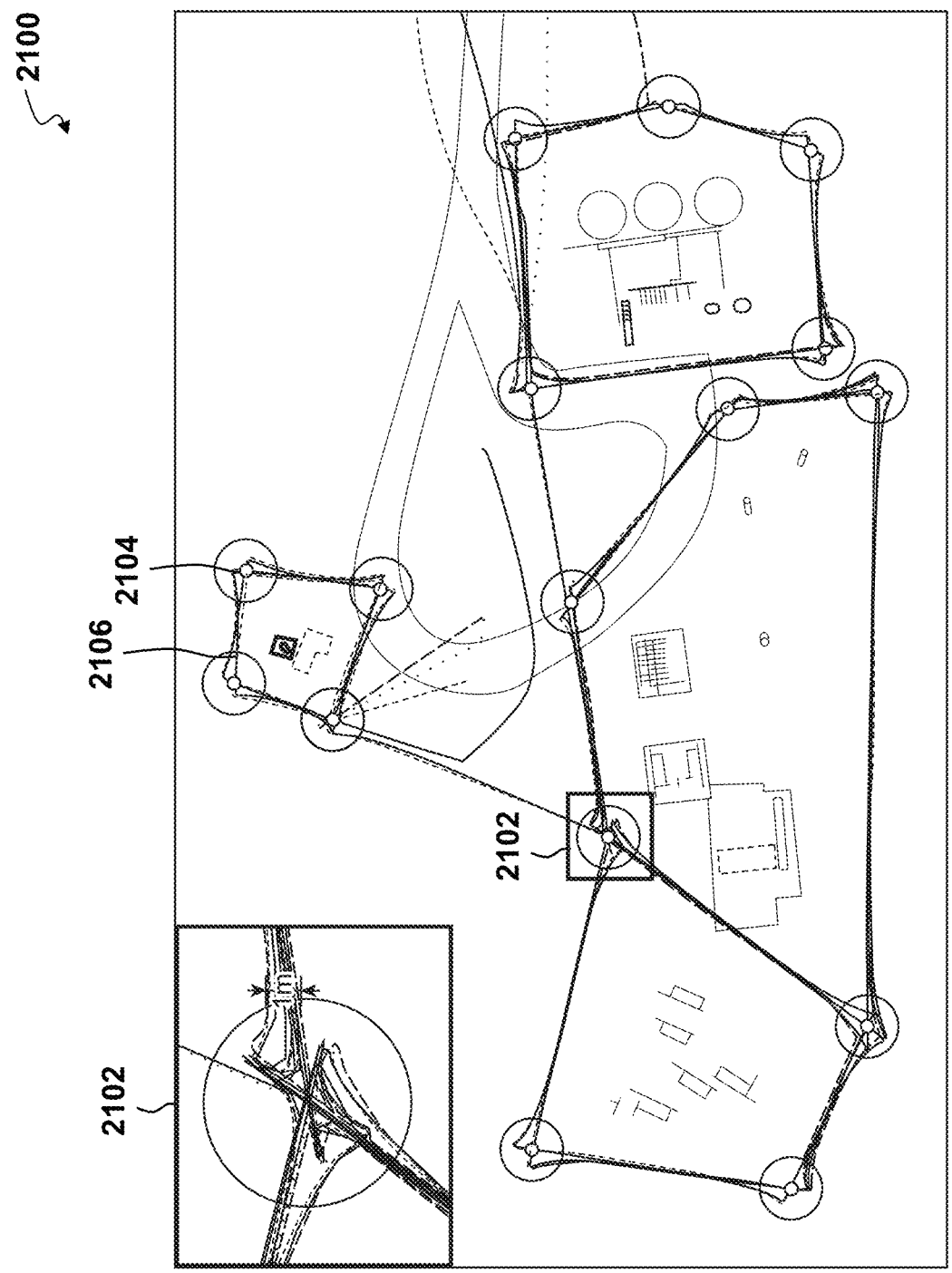
FIG. 21 depicts a resultant UAV trajectory based on the equipment grouping of FIG. 20, according to one embodiment.
Figure 22:
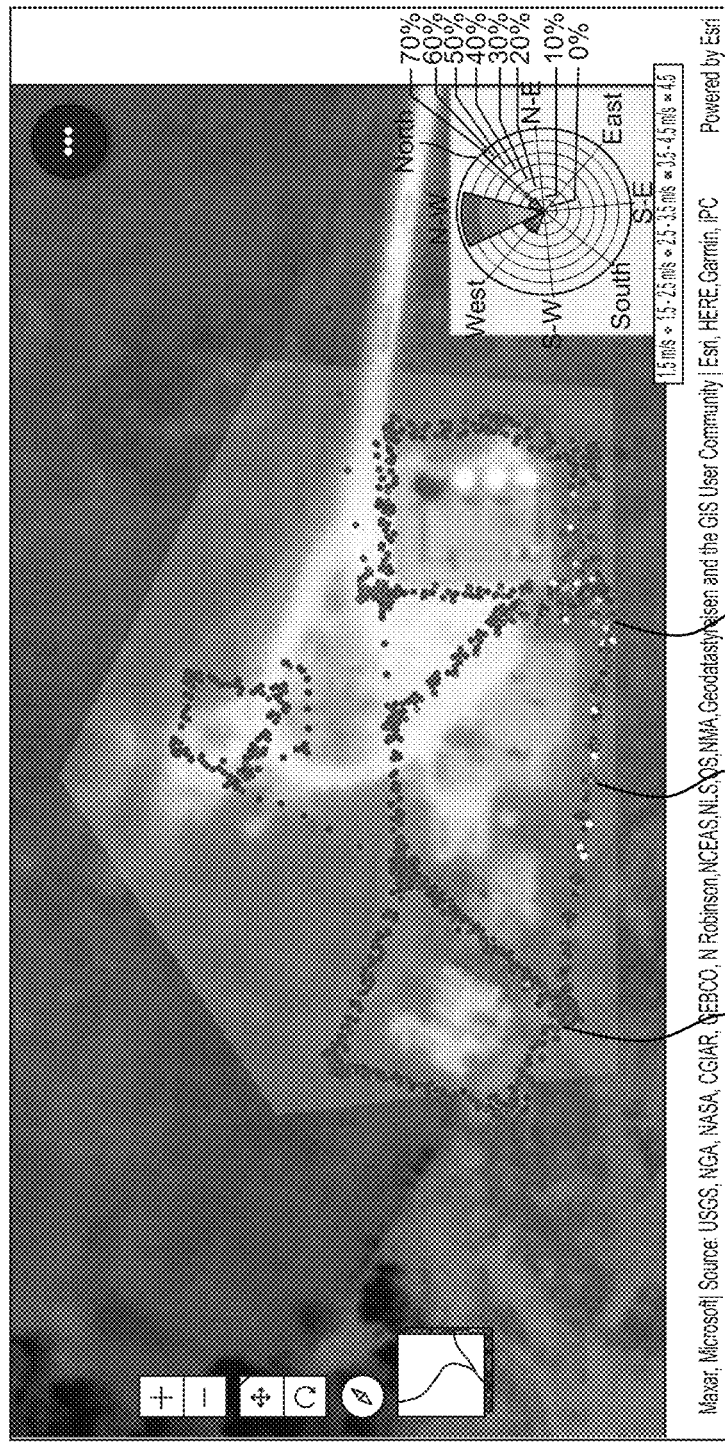
FIG. 22 depicts a resultant geo-rectified trace gas concentration data from the resultant UAV trajectory of FIG. 21, according to one embodiment.

The flight paths may be created based upon equipment or equipment grouping 2002, 2004, 2006, 2008 as shown in FIG. 20. The resultant drone trajectory 2100 given the equipment groups is shown in FIG. 21. The resultant geo-rectified trace gas concentration data from the fully enclosed flight paths 2200 are shown in FIG. 22.

Figure 23:
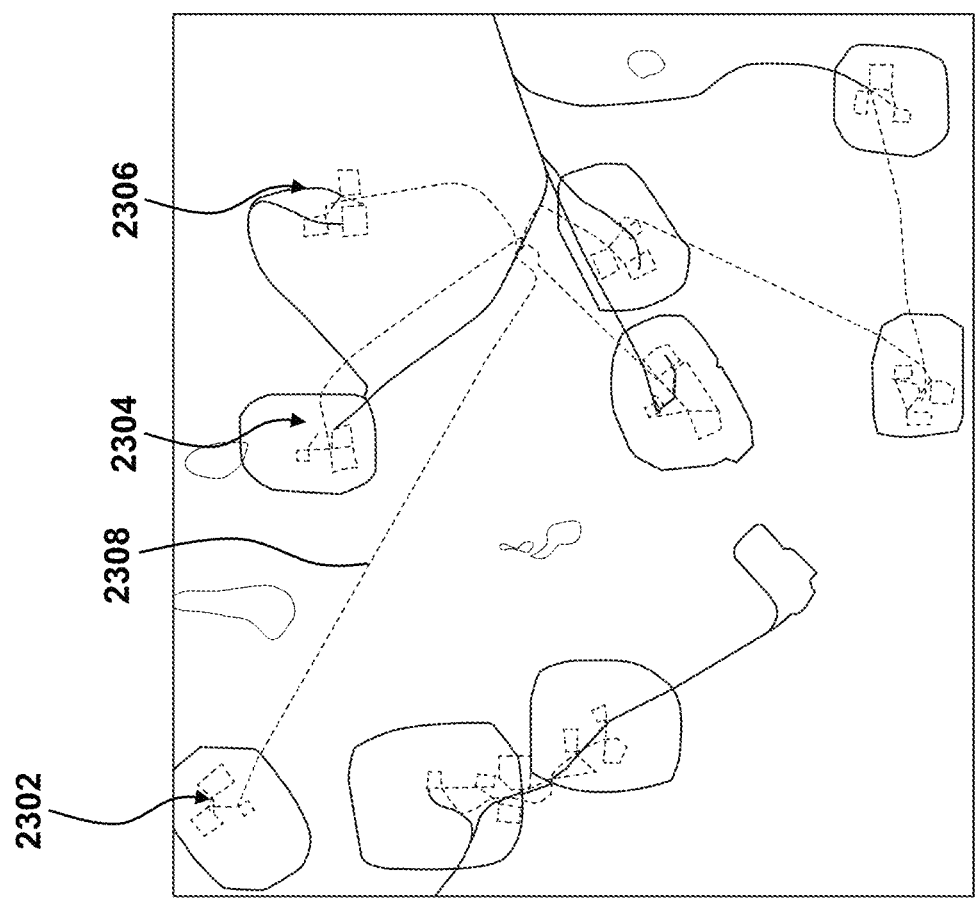
FIG. 23 depicts a flight path covering a series of fully or semi-enclosed flight paths that may be strewn together to be completed in a single flight, according to one embodiment.

A series of fully or semi-enclosed flight paths can be strewn together to be completed in a single flight as shown in FIG. 23), where the lines 2308 on the map shown the flight path 2300.

Figure 24:
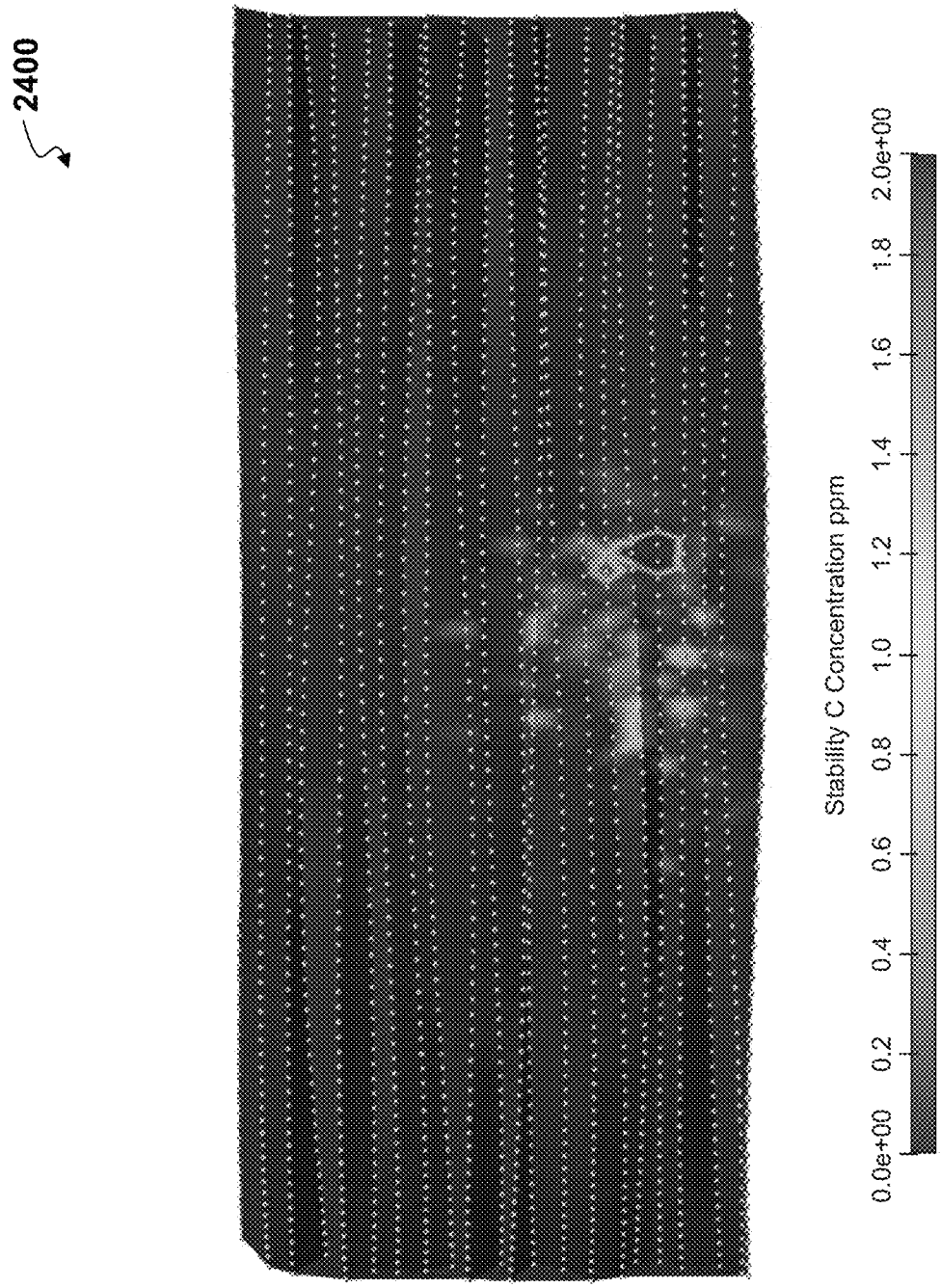
FIG. 24 depicts triangulation results with a flux surface projected, according to one embodiment.

With the additional value of flight path distance for each measurement point, the dataset can be transformed from a three dimensional representation to a two dimensional space with one axis being the flight path distance, and the other axis being the altitude. In this two-dimensional space, a Delaunay Triangulation can be calculated to yield a two dimensional surface in the two dimensional space where each measurement is connected to others with triangles to produce a contiguous manifold surface (FIG. 24). The triangulation defined by the relationships for the connections between measurement points can then be applied to the points represented in three dimensional space to produce a three dimensional contiguous manifold surface that connects all the measurement points.

Figure 25:
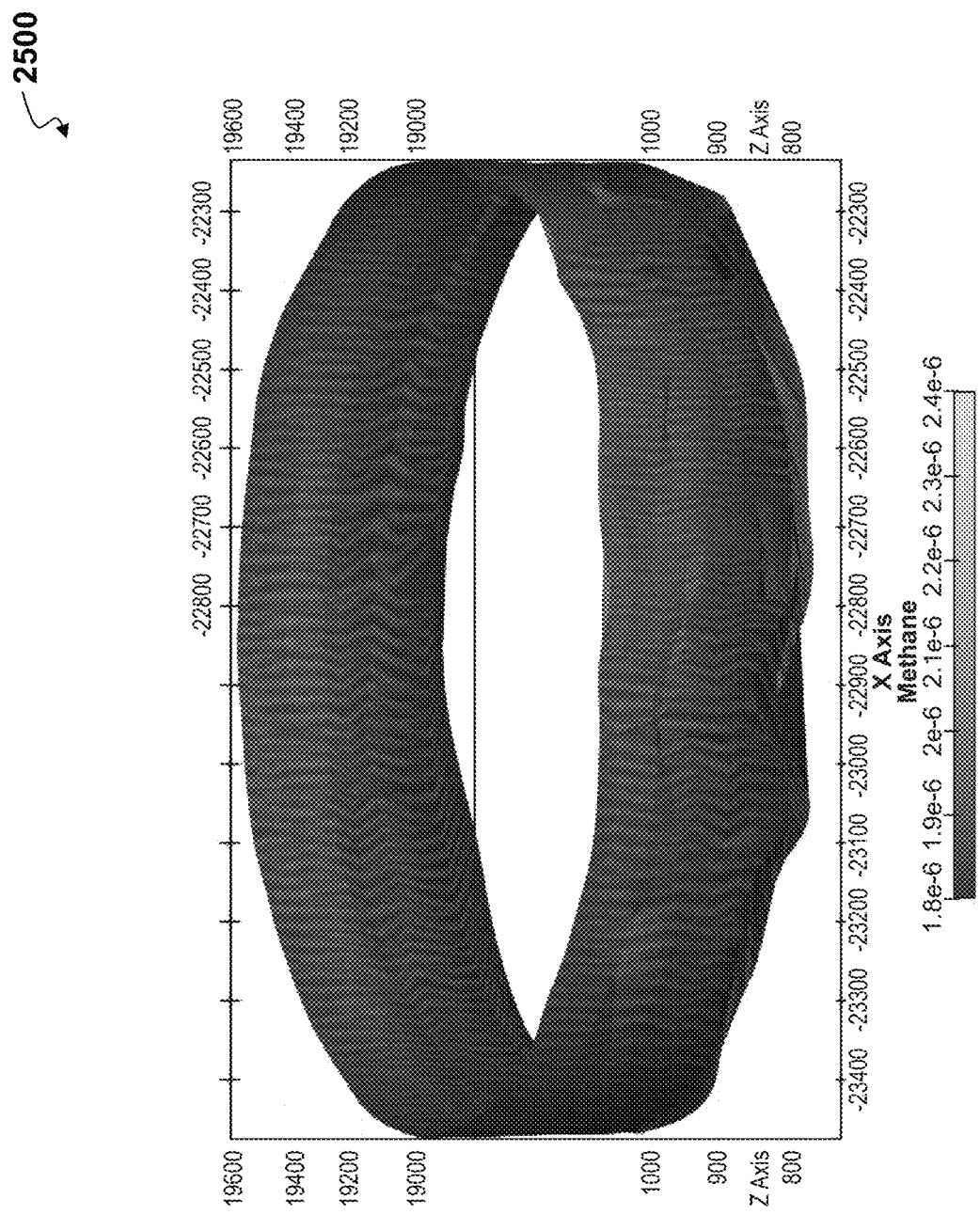
FIG. 25 depicts a fully enclosed triangulation with concentration, according to one embodiment.

In order to capture all the emissions on a site, flying a closed perimeter surface may be preferred (FIG. 25). If a flightpath completely encompasses the site, Gauss' Theorem may be applied directly to calculate the source rate within the flightpath perimeter using the concentration measurements at the perimeter. Due to operational constraints (access roads, power lines etc.), flying a fully closed flightpath may not always be possible, and so flying the perimeter with a small gap where flying is disallowed is an alternate approach (semi-Gauss).

Analyzing Gauss and semi-Gauss flights to extract a source rate requires application of computational geometry algorithms. Firstly, the dataset is taken from the aircraft and converted into Cartesian coordinates. The conversion is done using the Position Easting, Position Northing coordinates from the Extended Kalman Filter (EKF) as the X and Y components, and the LiDAR altitude from the LiDAR range finder for the Z component. Using the EKF outputs for location may allow for a more accurate measurement of location over using only GPS.

The dataset consists of point measurements made by the aerial vehicle in space. In order to deduce a source rate of gas emission, the individual flux values will have to be integrated over the whole dataset. Once the dataset has been converted into Cartesian space, it is necessary to triangulate the point measurements so that a continuous surface is available to perform the surface integral on (dS).

$$\iiint_V (\nabla \cdot F) dV = \oiint_S (F \cdot n) dS$$

The disclosed system and method for generating the continuous surface is disclosed herein. Delaunay Triangulation algorithms create a two-dimensional triangulation (surface) from a two-dimensional dataset, but may not be able to create a two-dimensional triangulation (surface) from a three-dimensional dataset. Therefore, before applying a Delaunay Triangulation algorithm, the dataset may first be represented in two-dimensional space. For Gauss and semi-Gauss flightpaths, the dataset may be converted into altitude-s space, where altitude is the same dimension as in the three-dimensional dataset, and s is a new dimension measuring distance along the pass. For example, in a Gauss flightpath, the value of s monotonically increases along the pass, until the aerial vehicle reaches a determined point and then the value of s starts again from zero. This is akin to the distance along a lap. For a semi-Gauss flightpath, the value of s monotonically increases until the aerial vehicle reaches whatever obstacle it must avoid, and then makes a U-turn and backtracks along the same path (at a different altitude) while the value of s decreases. Both methods, including the identification of crossing a home point and detection of U-turn points are automatically processed.

Once the dataset is represented in altitude-s space, a Delaunay Triangulation is performed. The resulting triangulation is then applied on the dataset original Cartesian X, Y, Z space to produce a fully closed or semi-closed surface, with all the original scalar values (e.g. gas concentrations) intact.

In addition to the measurements made using the one or more gas concentration sensors mounted to the airframe, an anemometer is setup on-site at a suitable location to make unaffected wind measurements. As the aerial vehicle is sampling species concentrations, the anemometer is measuring instantaneous wind speed in three dimensions. These measurements are recorded at synchronized times as the species concentrations are made. An appropriate aerodynamic surface roughness length is chosen to represent the local ground conditions surrounding the measurement site.

The wind speed measurements taken by the anemometer are then extrapolated from the anemometer measurement altitude to the altitude of the aerial vehicle at that specific point in time. This may be done using the log-law boundary condition model for flows near rough boundaries. The wind direction remains uncorrected, and only the magnitude of the wind speed is scaled using the log-law. The altitude corrected wind vector from the anemometer is then assumed to be the wind vector at the location the gas concentration measurement is made. While this assumption that the wind is the same at two different points may not be physically accurate, it is a way to determine wind speed and direction at the measurement point. In moderate wind speed conditions, the stability of the atmospheric boundary layer increases, resulting in less wind variance, therefore giving better correlation between the anemometer measurement and the wind at the sensor.

With the surface now created, a surface normal unit vector can be calculated at each point in the dataset. By performing the dot product of the surface normal vector and the wind vector, a volumetric flux rate of airflow is calculated for every point on the surface. This represents how many $m^3$ of air is entering or leaving the control volume per $m^2$ (dS).

In order to provide accurate relative gas measurements, a high pass filter is applied over the input concentration measurements. The filter removes any low frequency sensor drift, while still resolving all details from emissions. The time constant chosen for the filter is based on analysis of the sensor stability.

Multiplying the above wind flux values by the volume fraction of gas ($m^3$ $CH_4$ or $CO_2/m^3$ air) gives the volumetric flux rate of gas at each point ($m^3$ gas/s/$m^2$ area).

Because the control surface does not completely encompass the control volume, and the measurements were not taken at the exact same time (therefore wind may vary during flight), the standard incompressible equation of continuity does not hold true.

$$\nabla \cdot u \neq 0$$

This means that the net flux cannot simply be calculated by integrating the point gas flux measurements across the entire surface. Instead, a more piecemeal approach must be taken. To calculate the flux of gas entering the control volume, the surface is thresholded to where wind is flowing into the control volume only. With this surface, the volumetric flux rate of gas can be integrated to give the total inward volumetric flux of gas into the control volume ($m^3$ species/s).

$$\text{volumetric flowrate averaging} = \frac{\int_A \frac{dc}{\partial A} dA}{\int_A \frac{du}{\partial A} dA}$$

Once the species flux rate has been established, a total air volumetric rate must be calculated as well. The volumetric rate calculation may be done by integrating the wind velocity normal component to give a total air volumetric flux rate. By dividing the species volumetric flux rate by the air volumetric flux rate, the volumetric flowrate averaged inflowing species concentration is calculated.

A similar solution could be obtained by averaging all the values of volumetric flux rate of gas at each point, but the triangulation of the real-world dataset yields varied triangles, and this difference in size should be considered when calculating the average incoming volumetric gas flux rate. This process to get the total background concentration value is volumetric flow averaging and is necessary for calculating convective quantities such as species concentrations. In this case, the integral operator is not commutative because the wind values vary on the surface, and therefore the two integrals must be performed separately, and their results divided together.

The volumetric-flow-rate averaged concentration of the inflowing gas can then be subtracted from the concentration values measured where anemometry indicates gas is flowing out of the control volume. The resulting values are the enhanced concentrations with the background concentration component removed.

With the enhanced concentration values, the final net flux rate can be calculated. By again multiplying the component of wind velocity normal to the control surface by the concentration enhancement, the flux rate of the enhanced species concentration per unit area is obtained ($m^3$ species/$m^2$/second). Integrating this across the whole of the outflowing area This disclosed approach has the benefit that it satisfies the fundamental fluid dynamics equation for flow of a species through a control volume. Continuity of the species is used to ensure that all of the concentration upstream is subtracted from the concentration downstream, even if the oncoming flow has not got a uniform concentration of gas. Because the control volume is still open at the top, and the discrete sampling process means that there are gaps in the control surface, absolute integrals of continuity of mass and continuity of species cannot be simply applied. In addition, sampling all the points non-simultaneously, and in transient wind conditions, means that flux through any point in the control surface is constantly changing.

Despite fully considering the background concentration into calculations, there may still be a significant degree of error incurred from wind speed measurement. One process may utilize a ground weather station, that is set-up on site in a location with the least amount of interference from other obstacles as possible. Even in the optimal location, the anemometer is not co-located with the aerial vehicle at any time, and so the reading at the anemometer will be different from the actual wind-speed at the drone. This effect is particularly strong during light wind conditions, as a small change in the wind speed can incur a large change in the concentration values measured. In light wind conditions, the atmospheric boundary layer is also more unstable, resulting in more diffusion of the species plume, and therefore lower concentration values than with a more consistent wind.

Wind Direction and Vertical Gradient

Figure 11:
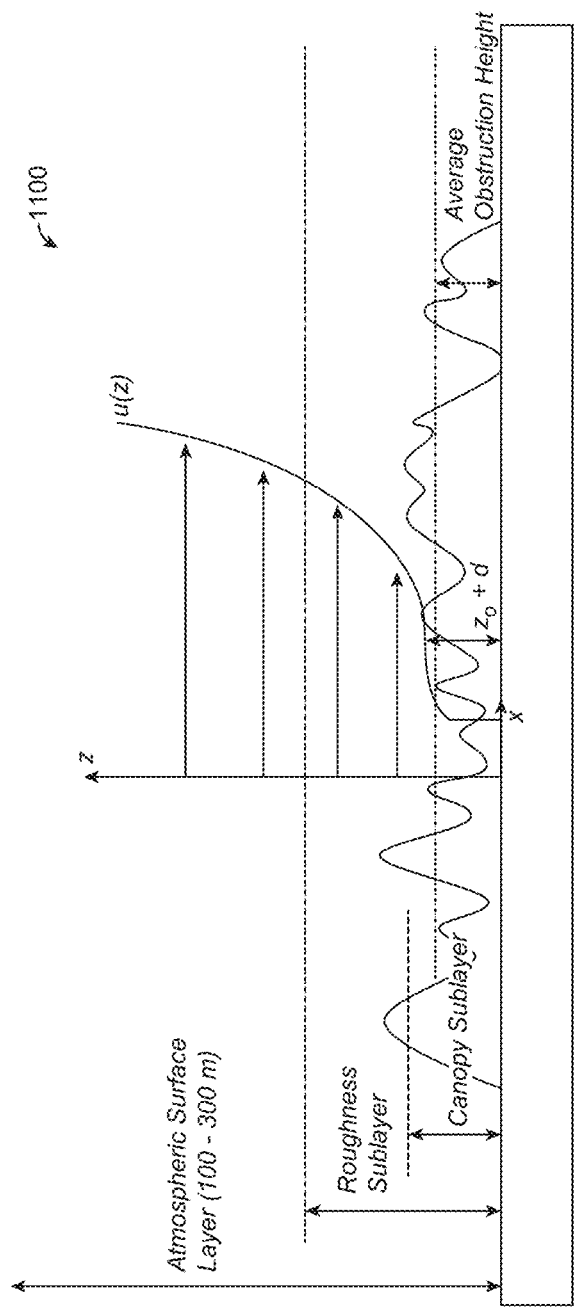
FIG. 11 depicts a diagram illustrating the primary surface level sublayers in the Atmospheric Boundary Layer, according to one embodiment.

FIG. 11 depicts a diagram 1100 illustrating the primary surface level sublayers in the Atmospheric Boundary Layer, according to one embodiment. An important input to the Emissions Estimate model disclosed herein is wind speed. Most of the measurements made by the disclosed UAS will be performed within the Roughness Sublayer portion of the atmospheric sublayer, i.e., the region from the surface to just above the average obstruction height or the local topography. In this region, the standard log law vertical wind gradient model provides a reasonable approximation of the vertical wind profile. Vertical wind profile may be approximated using a log law. Other ways of determining the vertical wind profile given the wind at a certain height and projected altitude are possible and contemplated. In some embodiments, the vertical wind profile may be measured directly. The vertical wind gradient or the vertical wind model may be determined based on the meteorological data measured, recorded, and/or predicted.

Figure 12B:
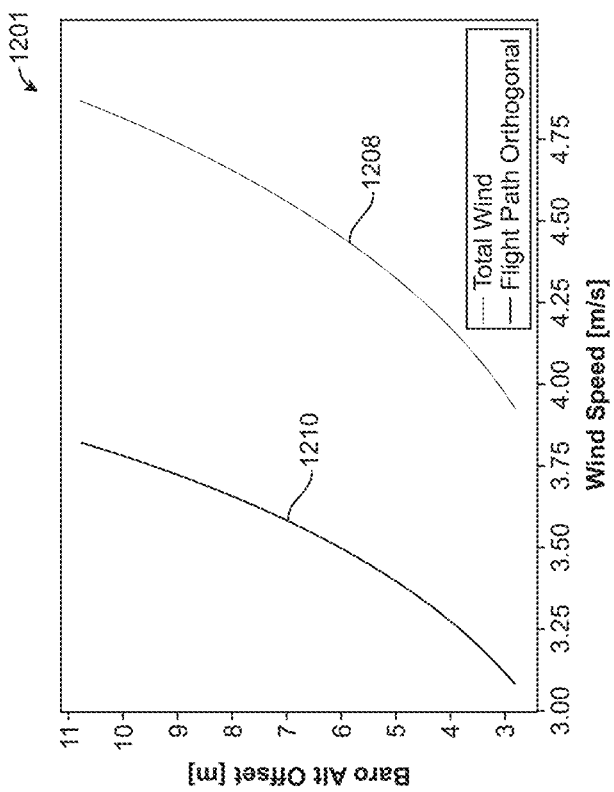
FIG. 12B depicts a modeled wind profile for the total wind and the derived orthogonal wind.
Figure 12A:
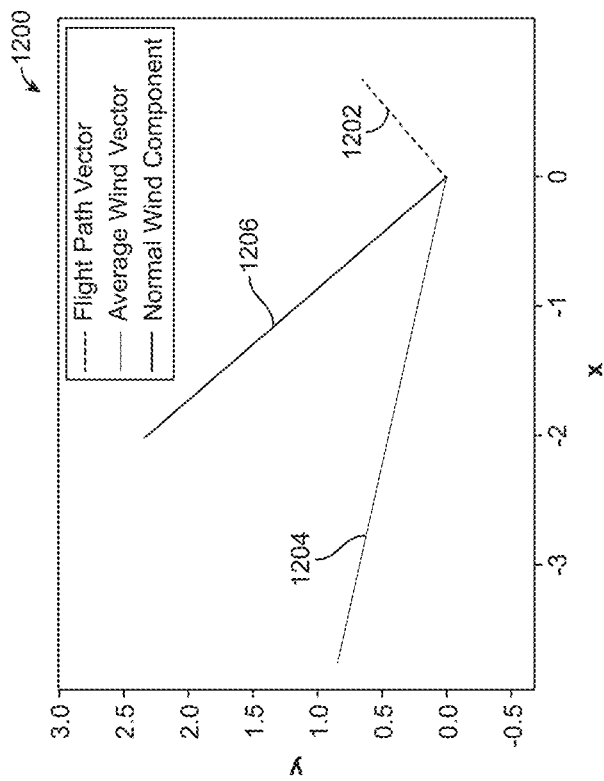
FIG. 12A depicts a flux plane average flight path vector, average wind vector, and derived normal wind component, according to one embodiment.

FIG. 12A depicts a graph 1200 of a flux plane average flight path vector 1202, average wind vector 1204, and derived normal wind component 1206, according to one embodiment. FIG. 12B depicts a graph 1201 of a modeled wind profile for the total wind 1208 and the derived orthogonal wind 1210. The Emissions Estimate algorithm determines the surface wind speed and direction utilizing measurements from the onsite 2D or 3D sonic anemometer. Due to local wind variability, it is necessary to derive the average and/or median normal wind component to the flown flight path surface. The orthogonal wind component is utilized to model the local wind profile. The derived orthogonal wind profile 1210 is utilized in the emissions calculation.

Emissions Calculation

Figure 13:
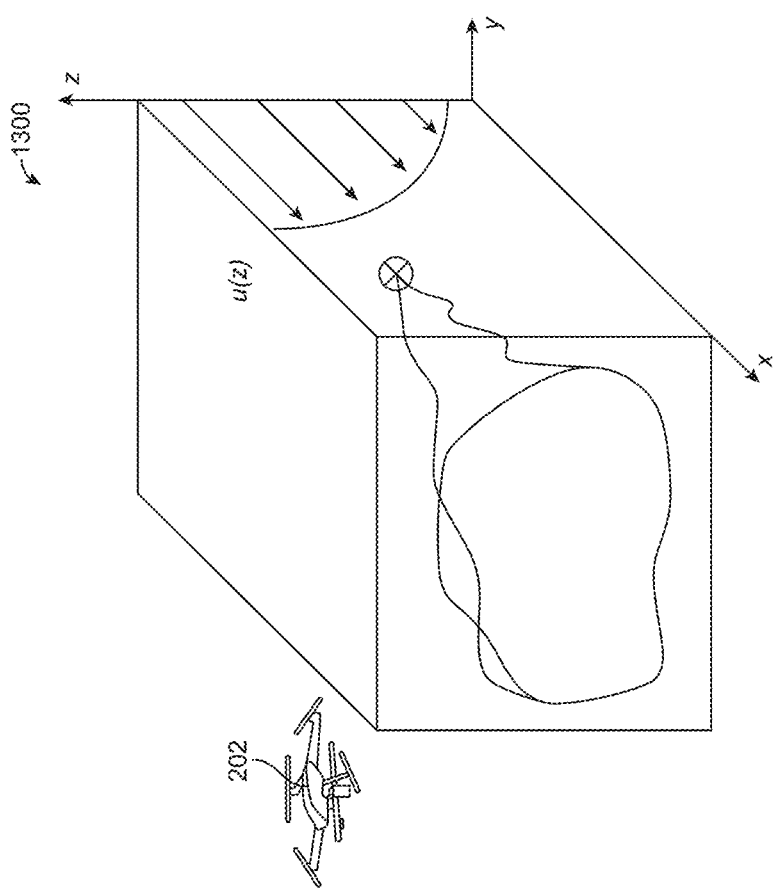
FIG. 13 depicts a schematic drawing of an Emissions Estimate Model, according to one embodiment.

FIG. 13 depicts a schematic drawing 1300 of an Emissions Estimate Model, according to one embodiment. The Emissions Estimate algorithm is based on an engineering control volume model. This means that the two key inputs to the model are the concentration profile on the outflow surface (or flight path surface), and the wind speed through the outflow. The concentration enhancement is measured by the disclosed sensor in volumetric concentration units, i.e., ppmv. To determine the source emission rate, it is necessary to convert from volumetric concentration to mass concentration, this is accomplished through the ideal gas law. The ideal gas law is used to calculate the air density based on the local air temperature and atmospheric pressure. At or below about 1% trace-gas in air, the contribution of trace-gas to the overall mixture density is negligible, i.e. the change in specific gravity of the mixture is small. For trace-gas concentrations less than 10,000 ppmv, the mass concentration of trace-gas can be obtained by multiplying the volumetric concentration measurement by the air density to yield $kg_{CH4}/m^3$. In the ideal gas law, the state of an amount of gas is determined by its pressure, volume, and temperature.

After converting the concentration enhancement to mass units and multiplying the concentration surface by the altitude dependant wind, a 2D integration over the entire surface is performed to arrive at the mass flux through the surface (Eq. 1) in units of kg/s. The velocity (u) is at a given altitude (z). A concentration (c) is at the distance Gamma (γ) and altitude (z). The concentration (c) is a function of Gamma (γ) along the flight path and altitude (z).

$$\iint u(z)c(\gamma,z)d\gamma dz \qquad \text{Eq. 1}$$

Figure 14:
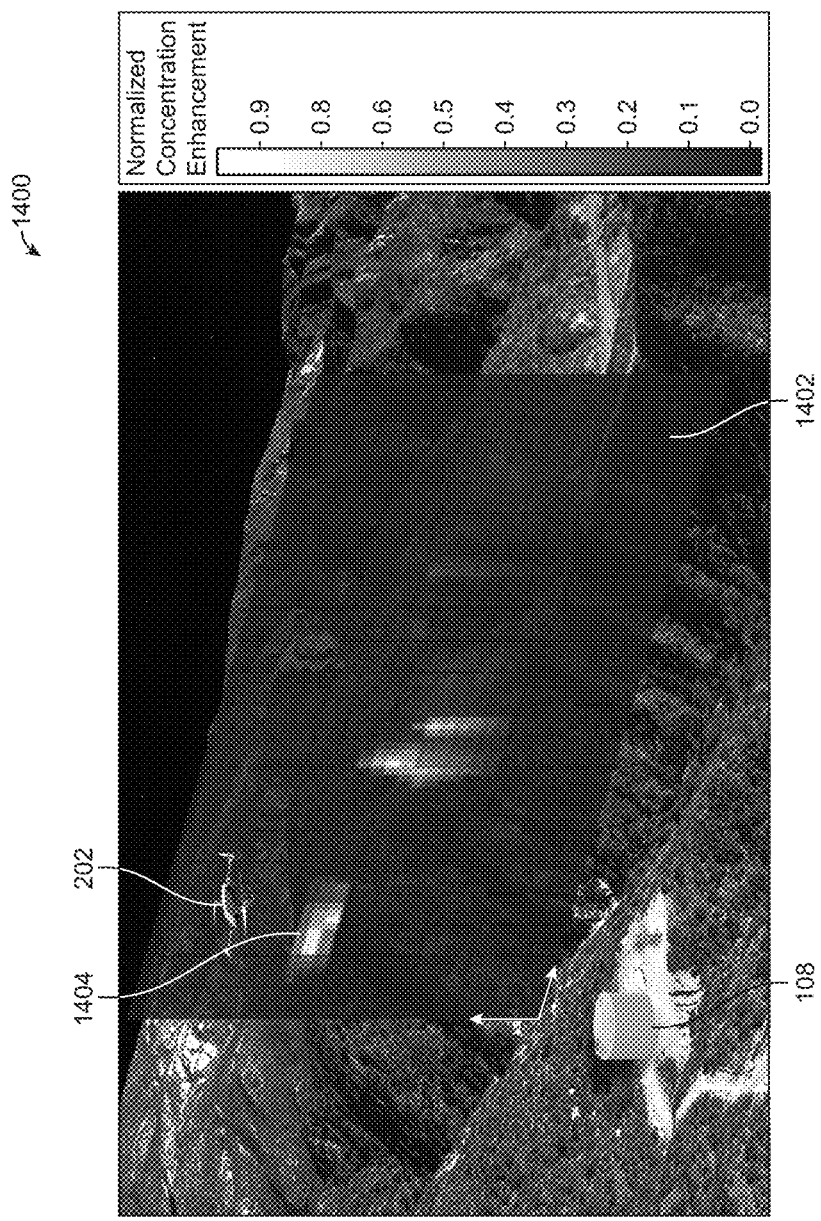
FIG. 14 depicts a 3-dimensional illustration of a UAS system Emissions measurement process, according to one embodiment.

FIG. 14 depicts a 3-dimensional illustration of a UAS system Emissions measurement process 1400, according to one embodiment. The UAV 202 flies vertical, cross-wind transects downwind of potential trace-gas sources 108 and measures ambient trace-gas concentration. Elevated trace-gas concentration is the signature of an upwind source. The measurements are interpolated onto a continuous grid 1402, multiplied by the corresponding wind vector, and spatially integrated to quantify the source emission rates.

Figure 15:
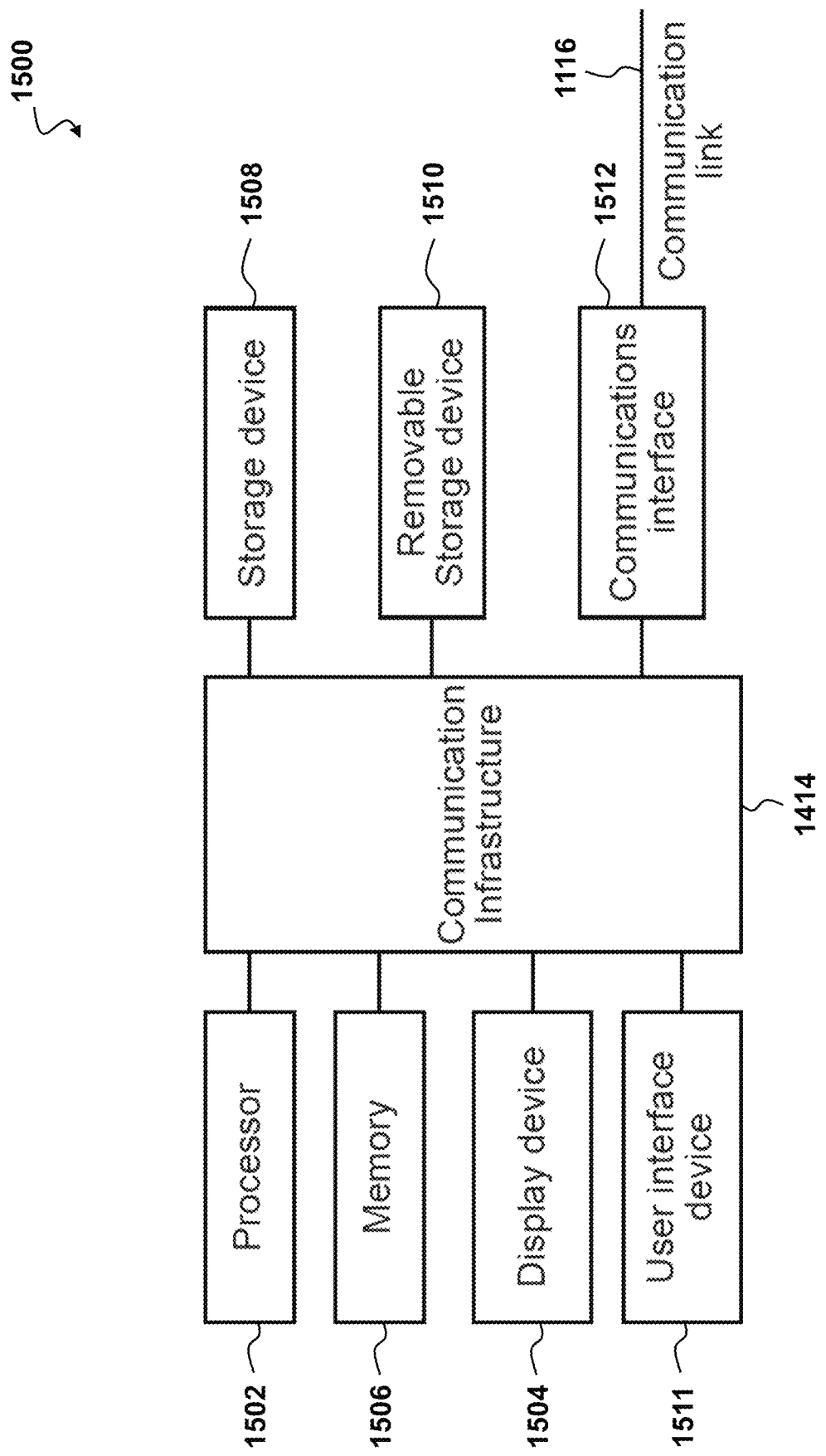
FIG. 15 shows a high-level block diagram and process of a computing system for implementing an embodiment of the system and process.

FIG. 15 is a high-level block diagram 1500 showing a computing system comprising a computer system useful for implementing an embodiment of the system and process, disclosed herein. Embodiments of the system may be implemented in different computing environments. The computer system includes one or more processors 1502, and can further include an electronic display device 1504 (e.g., for displaying graphics, text, and other data), a main memory 1506 (e.g., random access memory (RAM)), storage device 1508, a removable storage device 1510 (e.g., removable storage drive, a removable memory module, a magnetic tape drive, an optical disk drive, a computer readable medium having stored therein computer software and/or data), user interface device 1511 (e.g., keyboard, touch screen, keypad, pointing device), and a communication interface 1512 (e.g., modem, a network interface (such as an Ethernet card), a communications port, or a PCMCIA slot and card). The communication interface 1512 allows software and data to be transferred between the computer system and external devices. The system further includes a communications infrastructure 1514 (e.g., a communications bus, cross-over bar, or network) to which the aforementioned devices/modules are connected as shown.

Information transferred via communications interface 1514 may be in the form of signals such as electronic, electromagnetic, optical, or other signals capable of being received by communications interface 1514, via a communication link 1516 that carries signals and may be implemented using wire or cable, fiber optics, a phone line, a cellular/mobile phone link, an radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process.

Embodiments have been described with reference to flowchart illustrations and/or block diagrams of methods, apparatus (systems) and computer program products according to embodiments. Each block of such illustrations/diagrams, or combinations thereof, can be implemented by computer program instructions. The computer program instructions when provided to a processor produce a machine, such that the instructions, which execute via the processor, create means for implementing the functions/operations specified in the flowchart and/or block diagram. Each block in the flowchart/block diagrams may represent a hardware and/or software module or logic, implementing embodiments. In alternative implementations, the functions noted in the blocks may occur out of the order noted in the figures, concurrently, etc.

Computer programs (i.e., computer control logic) are stored in main memory and/or secondary memory. Computer programs may also be received via a communications interface 1512. Such computer programs, when executed, enable the computer system to perform the features of the embodiments as discussed herein. In particular, the computer programs, when executed, enable the processor and/or multi-core processor to perform the features of the computer system. Such computer programs represent controllers of the computer system.

Figure 16:
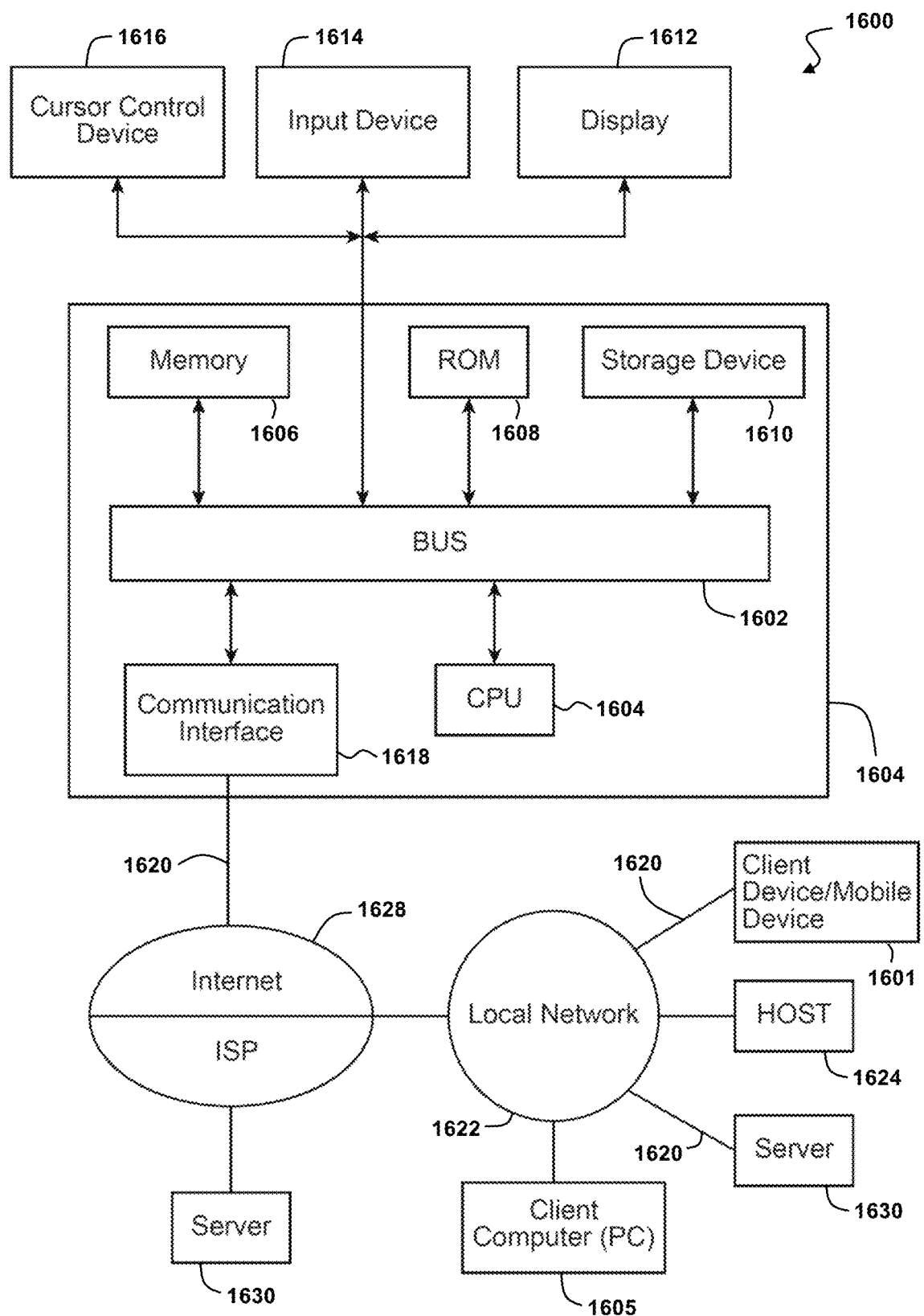
FIG. 16 shows a block diagram and process of an exemplary system in which an embodiment may be implemented.

FIG. 16 shows a block diagram of an example system 1600 in which an embodiment may be implemented. The system 1600 includes one or more client devices 1601 such as consumer electronics devices, connected to one or more server computing systems 1630. A server 1630 includes a bus 1602 or other communication mechanism for communicating information, and a processor (CPU) 1604 coupled with the bus 1602 for processing information. The server 1630 also includes a main memory 1606, such as a random access memory (RAM) or other dynamic storage device, coupled to the bus 1602 for storing information and instructions to be executed by the processor 1604. The main memory 1606 also may be used for storing temporary variables or other intermediate information during execution or instructions to be executed by the processor 1604. The server computer system 1630 further includes a read only memory (ROM) 1608 or other static storage device coupled to the bus 1602 for storing static information and instructions for the processor 1604. A storage device 1610, such as a magnetic disk or optical disk, is provided and coupled to the bus 1602 for storing information and instructions. The bus 1602 may contain, for example, thirty-two address lines for addressing video memory or main memory 1606. The bus 1602 can also include, for example, a 32-bit data bus for transferring data between and among the components, such as the CPU 1604, the main memory 1606, video memory and the storage 1610. Alternatively, multiplex data/address lines may be used instead of separate data and address lines.

The server 1630 may be coupled via the bus 1602 to a display 1612 for displaying information to a computer user. An input device 1614, including alphanumeric and other keys, is coupled to the bus 1602 for communicating information and command selections to the processor 1604. Another type or user input device comprises cursor control 1616, such as a mouse, a trackball, or cursor direction keys for communicating direction information and command selections to the processor 1604 and for controlling cursor movement on the display 1612.

According to one embodiment, the functions are performed by the processor 1604 executing one or more sequences of one or more instructions contained in the main memory 1606. Such instructions may be read into the main memory 1606 from another computer-readable medium, such as the storage device 1610. Execution of the sequences of instructions contained in the main memory 1606 causes the processor 1604 to perform the process steps described herein. One or more processors in a multi-processing arrangement may also be employed to execute the sequences of instructions contained in the main memory 1606. In alternative embodiments, hard-wired circuitry may be used in place of or in combination with software instructions to implement the embodiments. Thus, embodiments are not limited to any specific combination of hardware circuitry and software.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allow a computer to read such computer readable information. Computer programs (also called computer control logic) are stored in main memory and/or secondary memory. Computer programs may also be received via a communications interface. Such computer programs, when executed, enable the computer system to perform the features of the embodiments as discussed herein. In particular, the computer programs, when executed, enable the processor multi-core processor to perform the features of the computer system. Accordingly, such computer programs represent controllers of the computer system.

Generally, the term "computer-readable medium" as used herein refers to any medium that participated in providing instructions to the processor 1604 for execution. Such a medium may take many forms, including but not limited to, non-volatile media, volatile media, and transmission media. Non-volatile media includes, for example, optical or magnetic disks, such as the storage device 1610. Volatile media includes dynamic memory, such as the main memory 1606. Transmission media includes coaxial cables, copper wire and fiber optics, including the wires that comprise the bus 1602. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, an EPROM, a FLASH-EPROM, any other memory chip or cartridge, a carrier wave as described hereinafter, or any other medium from which a computer can read.

Various forms of computer readable media may be involved in carrying one or more sequences of one or more instructions to the processor 1604 for execution. For example, the instructions may initially be carried on a magnetic disk of a remote computer. The remote computer can load the instructions into its dynamic memory and send the instructions over a telephone line using a modem. A modem local to the server 1630 can receive the data on the telephone line and use an infrared transmitter to convert the data to an infrared signal. An infrared detector coupled to the bus 1602 can receive the data carried in the infrared signal and place the data on the bus 1602. The bus 1602 carries the data to the main memory 1606, from which the processor 1604 retrieves and executes the instructions. The instructions received from the main memory 1606 may optionally be stored on the storage device 1610 either before or after execution by the processor 1604.

The server 1630 also includes a communication interface 1618 coupled to the bus 1602. The communication interface 1618 provides a two-way data communication coupling to a network link 1620 that is connected to the world wide packet data communication network now commonly referred to as the Internet 1628. The Internet 1628 uses electrical, electromagnetic or optical signals that carry digital data streams. The signals through the various networks and the signals on the network link 1620 and through the communication interface 1618, which carry the digital data to and from the server 1630, are exemplary forms or carrier waves transporting the information.

In another embodiment of the server 1630, interface 1618 is connected to a network 1622 via a communication link 1620. For example, the communication interface 1618 may be an integrated services digital network (ISDN) card or a modem to provide a data communication connection to a corresponding type of telephone line, which can comprise part of the network link 1620. As another example, the communication interface 1618 may be a local area network (LAN) card to provide a data communication connection to a compatible LAN. Wireless links may also be implemented. In any such implementation, the communication interface 1618 sends and receives electrical electromagnetic or optical signals that carry digital data streams representing various types of information.

The network link 1620 typically provides data communication through one or more networks to other data devices. For example, the network link 1620 may provide a connection through the local network 1622 to a host computer 1624 or to data equipment operated by an Internet Service Provider (ISP). The ISP in turn provides data communication services through the Internet 1628. The local network 1622 and the Internet 1628 both use electrical, electromagnetic or optical signals that carry digital data streams. The signals through the various networks and the signals on the network link 1620 and through the communication interface 1618, which carry the digital data to and from the server 1630, are exemplary forms or carrier waves transporting the information.

The server 1630 can send/receive messages and data, including e-mail, program code, through the network, the network link 1620 and the communication interface 1618. Further, the communication interface 1618 can comprise a USB/Tuner and the network link 1620 may be an antenna or cable for connecting the server 1630 to a cable provider, satellite provider or other terrestrial transmission system for receiving messages, data and program code from another source.

The example versions of the embodiments described herein may be implemented as logical operations in a distributed processing system such as the system 1600 including the servers 1630. The logical operations of the embodiments may be implemented as a sequence of steps executing in the server 1630, and as interconnected machine modules within the system 1600. The implementation is a matter of choice and can depend on performance of the system 1600 implementing the embodiments. As such, the logical operations constituting said example versions of the embodiments are referred to for e.g., as operations, steps or modules.

Similar to a server 1630 described above, a client device 1601 can include a processor, memory, storage device, display, input device and communication interface (e.g., e-mail interface) for connecting the client device to the Internet 1628, the ISP, or LAN 1622, for communication with the servers 1630.

The system 1600 can further include computers (e.g., personal computers, computing nodes) 1605 operating in the same manner as client devices 1601, wherein a user can utilize one or more computers 1605 to manage data in the server 1630.

Figure 17:
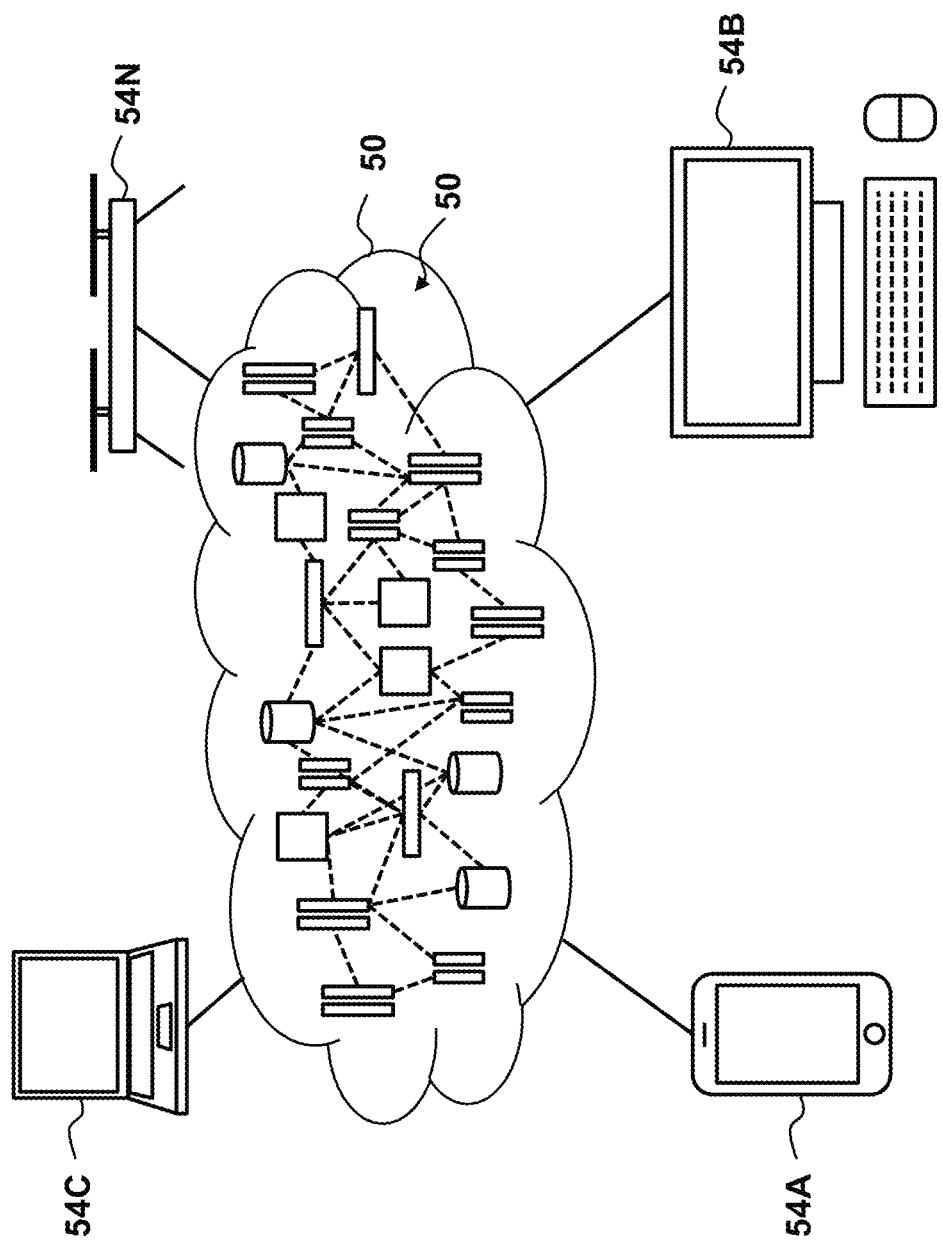
FIG. 17 depicts a cloud computing environment for implementing an embodiment of the system and process disclosed herein.

Referring now to FIG. 17, illustrative cloud computing environment 50 is depicted. As shown, cloud computing environment 50 comprises one or more cloud computing nodes 10 with which local computing devices used by cloud consumers, such as, for example, personal digital assistant (PDA), smartphone, smart watch, set-top box, video game system, tablet, mobile computing device, or cellular telephone 54A, desktop computer 54B, laptop computer 54C, and/or unmanned aerial system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 17 are intended to be illustrative only and that computing nodes 10 and cloud computing environment 50 can communicate with any type of computerized device over any type of network and/or network addressable connection (e.g., using a web browser).

Figure 18:
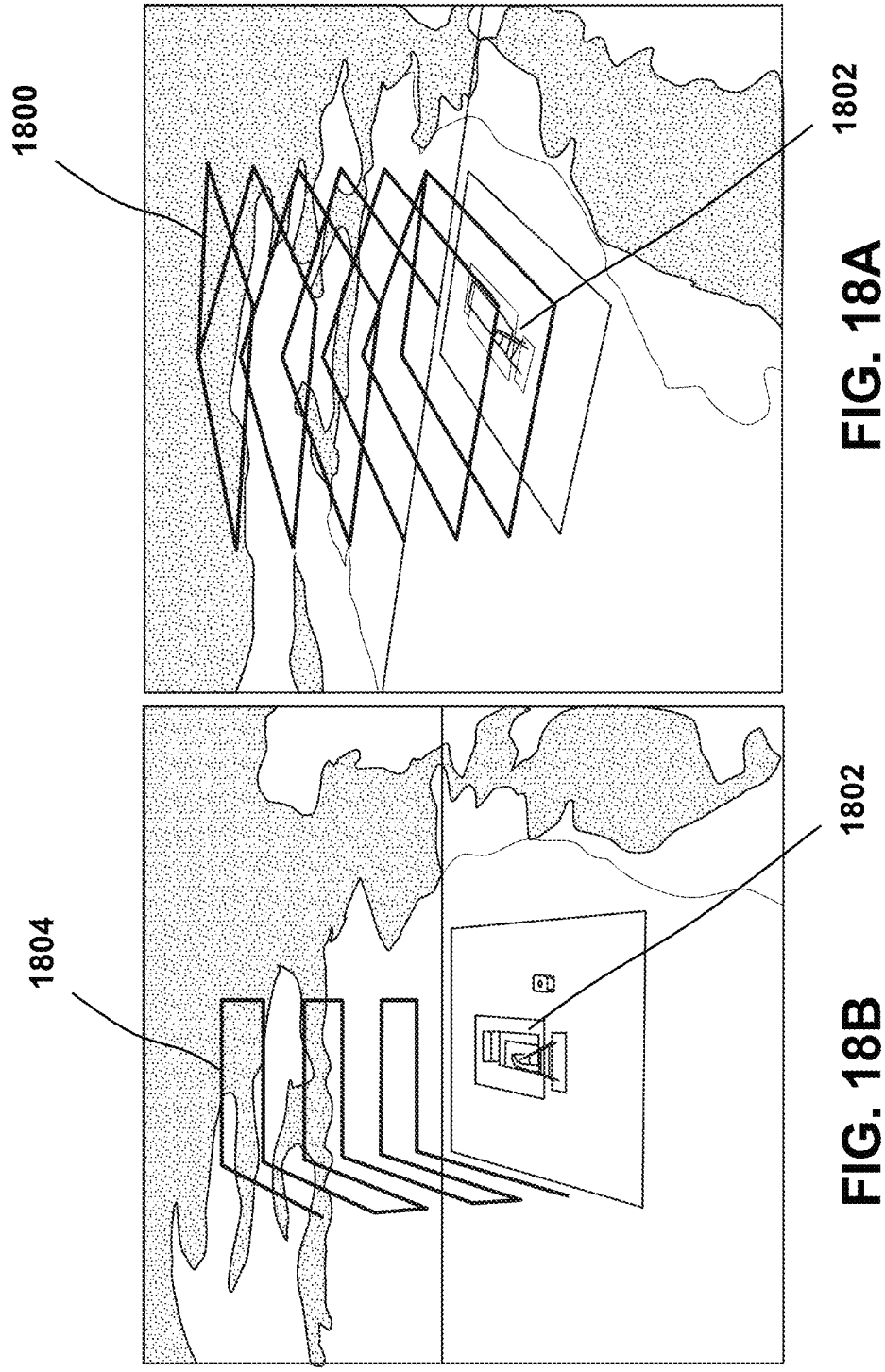
FIG. 18A depicts a flight path that fully circumnavigates a potential trace gas source, according to one embodiment.
FIG. 18B depicts a flight path that partially circumnavigates a potential trace gas source, according to one embodiment.

FIG. 18A depicts a flight path 1800 that fully circumnavigates a potential trace gas source 1802, according to one embodiment. FIG. 18B depicts a flight path 1804 that partially circumnavigates a potential trace gas source, according to one embodiment.

Figure 19:
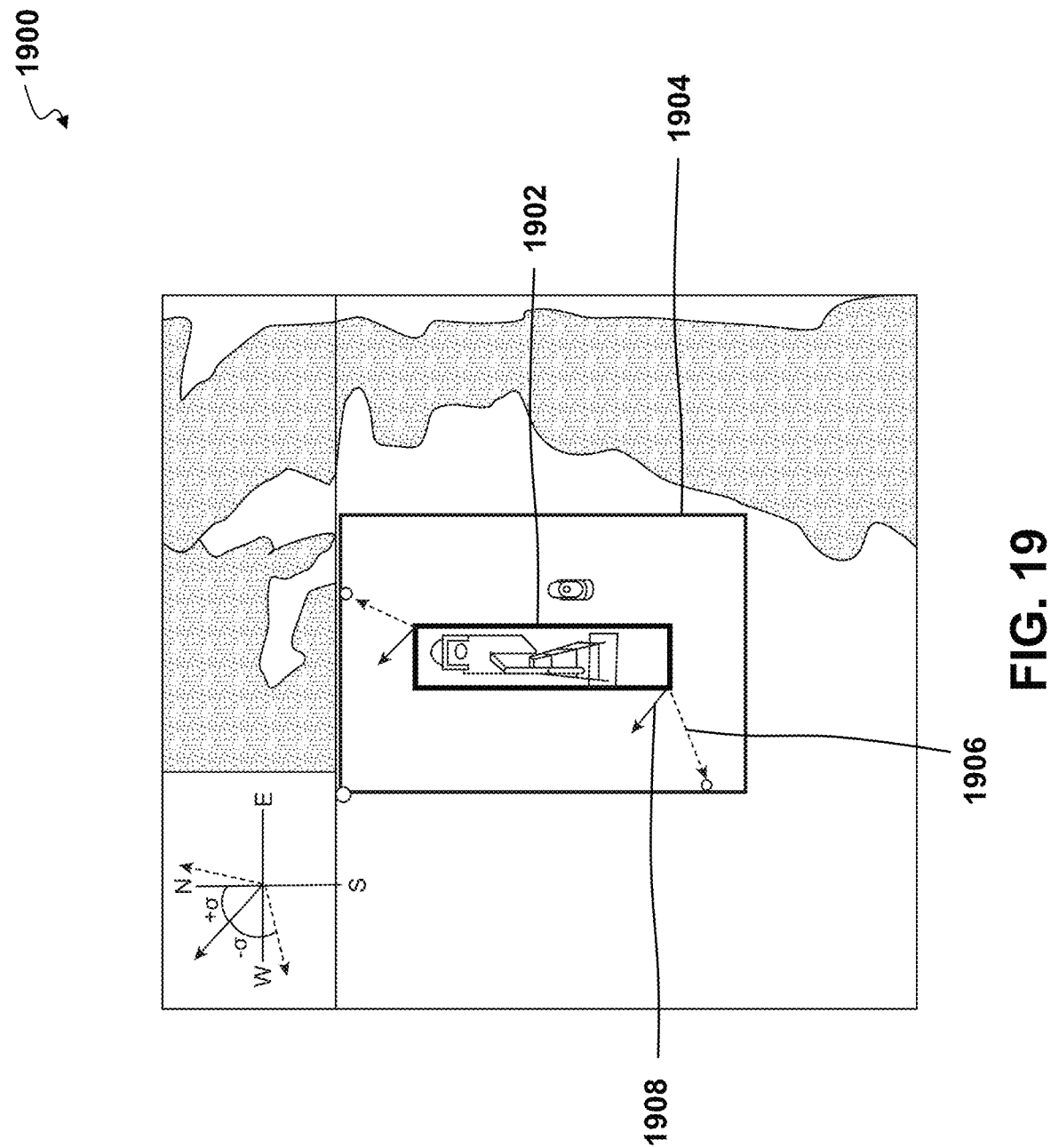
FIG. 19 depicts a top view of a circumnavigated flight path that can be generated by a series of flight lines that are a set distance from equipment being inspected, according to one embodiment.

FIG. 19 depicts a top view 1900 of a circumnavigated flight path 1904 that can be generated by a series of flight lines that are a set distance from equipment 1902 being inspected, according to one embodiment.

FIG. 20 depicts flight paths that may be created based upon equipment or equipment grouping, according to one embodiment. A location 2000 may include one or more survey groups 2002, 2004, 2006, 2008. Each survey group 2002, 2004, 2006, 2008 may include at least one equipment group 2018, 2020, 2024, 2026, 2028, 2030, 2034. The at least one equipment group 2018, 2020, 2024, 2026, 2028, 2030, 2034 may include potential trace gas sources, such as wellheads, flow lines, meter runs, manifolds, separators, tanks, or the like. The location 2000 may also include one or more obstacles 2010, 2012, 2014, 2016. The one or more obstacles 2010, 2012, 2014, 2016 may include stairs, SCADA, power lines, guard rails, or the like. A UAV may want to avoid or be required to avoid the one or more obstacles 2010, 2012, 2014, 2016 in the flight path.

FIG. 21 depicts a resultant UAV trajectory 2100 based on the equipment grouping of FIG. 20, according to one embodiment. A close-up view 2102 of a waypoint in the UAV trajectory 2100 is shown. The UAV may fly a flight path 2106 between waypoints 2104 in order to survey the equipment groups and detect any trace gas emissions from the potential trace gas sources.

FIG. 22 depicts a resultant geo-rectified trace gas concentration data 2200 from the resultant UAV trajectory of FIG. 21, according to one embodiment. Trace gas data may include measurements of no or almost no trace gas 2202, elevated trace gas measurements 2204, and high trace gas measurements 2206.

FIG. 23 depicts a flight path 2300 covering a series of fully or semi-enclosed flight paths that may be strewn together to be completed in a single flight, according to one embodiment. The flight path 2300 may cover several geographically separate locations 2302, 2304, 2306 that may be connected 2308 by flight paths. Each location 2302, 2304, 2306 may include one or more equipment groups, such as shown in FIG. 20.

FIG. 24 depicts triangulation results with a flux surface projected 2400, according to one embodiment.

FIG. 25 depicts a fully enclosed triangulation with concentration 2500, according to one embodiment.

FIG. 26 depicts a system 2600 for detecting trace gasses, according to one embodiment. The system may include one or more trace gas sensors located in one or more vehicles 2602, 2604, 2606, 2610. The one or more trace gas sensors may detect elevated trace gas concentrations from one or more potential gas sources 2620, 2622, such as a holding tank, pipeline, or the like. The potential gas sources 2620, 2622 may be part of a large facility, a small facility, or any location. The potential gas sources 2620, 2622 may be clustered and/or disposed distal from one another. The one or more trace gas sensors may be used to detect and quantify leaks of toxic gases, e.g., hydrogen disulfide, or environmentally damaging gases, e.g., methane, sulfur dioxide) in a variety of industrial and environmental contexts. Detection and quantification of these leaks are of interest to a variety of industrial operations, such as oil and gas, chemical production, and painting. Detection and quantification of leaks is also of value to environmental regulators for assessing compliance and for mitigating environmental and safety risks. In some embodiments, the at least one trace gas sensor may be configured to detect methane. In other embodiments, the at least one trace gas sensor may be configured to detect sulfur oxide, such as SO, SO2, SO3, S7O2, S6O2, S2O2, and the like. A trace gas leak 2624 may be present in a potential gas source 2620. The one or more trace gas sensors may be used to identify the trace gas leak 2624 and/or the source 2620 of the trace gas leak 2624 so that corrective action may be taken.

The one or more vehicles 2602, 2604, 2606, 2610 may include an unmanned aerial vehicle (UAV) 2602, an aerial vehicle 2604, a handheld device 2606, and a ground vehicle 2610. In some embodiments, the UAV 2602 may be a quadcopter or other device capable of hovering, making sharp turns, and the like. In other embodiments, the UAV 2602 may be a winged aerial vehicle capable of extended flight time between missions. The UAV 2602 may be autonomous or semi-autonomous in some embodiments. In other embodiments, the UAV 2602 may be manually controlled by a user. The aerial vehicle 2604 may be a manned vehicle in some embodiments. The handheld device 2606 may be any device having one or more trace gas sensors operated by a user 2608. In one embodiment, the handheld device 2606 may have an extension for keeping the one or more trace gas sensors at a distance from the user 2608. The ground vehicle 2610 may have wheels, tracks, and/or treads in one embodiment. In other embodiments, the ground vehicle 2610 may be a legged robot. In some embodiments, the ground vehicle 2610 may be used as a base station for one or more UAVs 2602. In some embodiments, one or more aerial devices, such as the UAV 2602, a balloon, or the like, may be tethered to the ground vehicle 2610. In some embodiments, one or more trace gas sensors may be located in one or more stationary monitoring devices 2626. The one or more stationary monitoring devices may be located proximate one or more potential gas sources 2620, 2622. In some embodiments, the one or more stationary monitoring devices may be relocated.

The one or more vehicles 2602, 2604, 2606, 2610 and/or stationary monitoring devices 2626 may transmit data including trace gas data to a ground control station (GCS) 2612. The GCS may include a display 2614 for displaying the trace gas concentrations to a GCS user 2616. The GCS user 2616 may be able to take corrective action if a gas leak 2624 is detected, such as by ordering a repair of the source 2620 of the trace gas leak. The GCS user 2616 may be able to control movement of the one or more vehicles 2602, 2604, 2606, 2610 in order to confirm a presence of a trace gas leak in some embodiments.

In some embodiments, the GCS 2612 may transmit data to a cloud server 2618. In some embodiments, the cloud server 2618 may perform additional processing on the data. In some embodiments, the cloud server 2618 may provide third party data to the GCS 2612, such as wind speed, temperature, pressure, weather data, or the like.

It is contemplated that various combinations and/or sub-combinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention herein disclosed by way of examples should not be limited by the particular disclosed embodiments described above.

What is claimed is:

1. A system, comprising:
   a trace-gas concentration sensor configured to be carried by an unmanned aerial vehicle (UAV), wherein the trace-gas concentration sensor is configured to generate trace-gas concentration data, which is included in a trace-gas data packet;
   a location sensor configured to generate location data comprising a trajectory of the trace-gas concentration sensor in space;
   one or more weather stations distal from the trace-gas concentration sensor, wherein each weather station generates a Meteorological data packet comprising weather data;
   a processor having addressable memory, the processor configured to:
      determine a control surface along a flight path of a UAV, wherein the control surface comprises a horizontal value that represents a distance along the control surface, wherein the control surface intersects an area downwind of a trace-gas source and circumnavigates the trace-gas source, wherein the control surface includes two or more first flight planes and one or more second flight planes, wherein the two or more first flight planes are substantially parallel to a ground surface, and wherein the one or more second flight planes are angled to connect two of the two or more first flight planes;
      receive the trace-gas data packet, wherein the trace-gas data packet comprises a trace-gas concentration data from the trace-gas concentration sensor and the location data for the trace-gas concentration sensor, wherein the location data is based on the horizontal value of the control surface along the flight path of the UAV;
      receive at least one Meteorological data packet from the one or more weather stations;
      combine the trace-gas data packet with a selected spatial and temporal Meteorological data packet; and
      determine a trace-gas emission rate of the trace-gas source based on the combined trace-gas data packet and the selected Meteorological data packet.

2. The system of claim 1 further comprising:
   a display in communication with the processor, wherein the display is configured to show the determined trace-gas emission rate of the trace-gas source on a map.

3. The system of claim 2, wherein the map is at least one of: a satellite image, an aerial image, a two-dimensional color map, a two-dimensional contour map, and a three-dimensional topographical surface.

4. The system of claim 1, wherein the processor is further configured to:
   determine the flight path of the UAV.

5. The system of claim 4, wherein the flight path of the UAV intersects an area downstream of the gas source and varies in horizontal distance perpendicular to an axis of a wind direction and an altitude.

6. The system of claim 1, further comprising:
   a payload of the trace-gas concentration sensor, wherein the payload comprises one or more in situ trace-gas concentration sensors configured to generate the trace-gas concentration data along the trajectory of the trace-gas concentration sensor in space.

7. The system of claim 6 wherein the location data comprises at least one of: a location of the trace-gas concentration sensor, a time corresponding to the location of the trace-gas concentration sensor, a barometric pressure, an altitude, a relative altitude, and an orientation of the trace-gas concentration sensor, and wherein the location data corresponds to the generated trace-gas concentration data along the trajectory of the trace-gas concentration sensor in space.

8. The system of claim 7 wherein the location of the at least one trace-gas concentration sensor is determined by at least one of: a global positioning system (GPS) and a location sensor.

9. The system of claim 7 wherein the location of the trace-gas concentration sensor further comprises a detection of at least one of: an absolute altitude of the trace-gas concentration sensor and a relative altitude of the trace-gas concentration sensor.

10. The system of claim 7 wherein the orientation of the trace-gas concentration sensor is determined by at least one of: an inertial measurement unit (IMU) and an orientation sensor.

11. The system of claim 1 wherein the trace-gas data packet comprises: a global positioning system (GPS) location of the trace-gas concentration sensor, a time, a barometric pressure, an altitude of the trace-gas concentration sensor, and an orientation of the trace-gas concentration sensor corresponding to the trace-gas concentration data.

12. The system of claim 1 wherein the Meteorological Data Packet comprises data from: an anemometer, one or more pressure sensors, a pryanometer, a ground temperature sensor, an air temperature sensor, and a current atmospheric condition sensor.

13. The system of claim 11 wherein at least one of: a ground control station (GCS), a cloud server, the trace-gas concentration sensor, and one or more weather stations comprises the processor.

14. The system of claim 1 wherein the determined trace-gas emission rate may be stored by at least one of: a ground control station (GCS), a cloud server, and one or more gas concentration sensors.

15. A method of determining a trace-gas emission rate using a system comprising one or more trace-gas concentration sensors generating trace-gas concentration data and a location sensor generating location data of the trace-gas concentration sensor in space, two or more weather stations distal from the trace-gas concentration sensor and generating weather data, and a processor having addressable memory, the method comprising:
determining a control surface along a flight path of an unmanned aerial vehicle (UAV), wherein the control surface comprises a horizontal value that represents a distance along the control surface, wherein the control surface intersects an area downwind of a trace-gas source and circumnavigates the trace-gas source, wherein the control surface includes two or more first flight planes and one or more second flight planes, wherein the two or more first flight planes are substantially parallel to a ground surface, and wherein the one or more second flight planes are angled to connect two of the two or more first flight planes;
receiving, by the processor, a UAV data packet from the UAV, wherein the UAV data packet comprises the trace-gas concentration data and UAV information covering locations of a UAV flight path, wherein the UAV information comprises a global positioning system (GPS) location of the one or more trace-gas concentration sensors corresponding to the trace-gas concentration data, wherein the location data is based on the horizontal value of the control surface along the flight path of the UAV;
receiving, by the processor, at least one Meteorological data packet from the two or more weather stations, wherein each weather station is distal from the UAV, wherein each weather station generates the Meteorological data packet comprising the weather data;
combining, by the processor, the UAV data packet with a nearest spatial and temporal Meteorological data packet; and
determining, by the processor, the trace-gas emission rate of a trace-gas source based on the combined UAV data packet and the nearest Meteorological data packet.

16. The method of claim 15 wherein the UAV flight path is controlled by a user via a ground control station (GCS).

17. The method of claim 15 further comprising:
measuring, by a payload of a UAV, the trace-gas concentration data along the UAV flight path, wherein the payload comprises one or more gas concentration sensors;
generating, by the UAV, the UAV data packet, wherein the UAV data packet comprises a spatial position of the UAV at each trace-gas concentration data measurement; and
generating, by the two or more weather stations of one or more weather stations, the Meteorological data packet;
wherein the UAV data packet comprises data from at least one of: a weather sensor, an onboard avionics, a barometric pressure sensor, an orientation sensor, an inertial measurement unit (IMU), a wireless radio, a global positioning system (GPS), a time measurement device, an altitude sensor, a location sensor, a radar, a lidar, an anemometer, and a Sonar; and
wherein the Meteorological data packet comprises data from: an anemometer, one or more pressure sensors, a pyranometer, a ground temperature sensor, an air temperature sensor, and a current atmospheric condition sensor.

18. A system, comprising:
one or more in-situ trace-gas concentration sensors connected to an unmanned aerial vehicle (UAV) configured to fly a UAV flight path and configured to generate the trace-gas concentration data measured along the UAV flight path, wherein the trace-gas concentration data is included in a UAV data packet;
one or more location sensors of the UAV configured to generate UAV information comprising a global positioning system (GPS) location of the UAV corresponding to the trace-gas concentration data measured along the UAV flight path, wherein the UAV information is included in the UAV data packet;
two or more weather stations distal from the UAV and configured to measure weather data and generate a Meteorological data packet comprising the weather data; and
a processor having addressable memory, the processor in communication with the UAV and the one or more weather stations, wherein the processor configured to:
determine a control surface along a flight path of a UAV, wherein the control surface comprises a horizontal value that represents a distance along the control surface, wherein the control surface intersects an area downwind of a trace-gas source and circumnavigates the trace-gas source, wherein the control surface includes two or more first flight planes and one or more second flight planes, wherein the two or more first flight planes are substantially parallel to a ground surface, and wherein the one or more second flight planes are angled to connect two of the two or more first flight planes;

receive the UAV data packet, from the UAV, comprising the trace-gas concentration data and UAV information comprising the location of the UAV, wherein the location of the UAV is based on the horizontal value of the control surface along the flight path of the UAV;

receive two or more Meteorological data packets from the two or more weather stations;

combine the UAV data packet with a nearest spatial and temporal Meteorological data packet;

determine a trace-gas emission rate of a trace-gas source based on the combined UAV data packet and the nearest Meteorological data packet; and show the determined trace-gas emission rate of the trace-gas source on a map via a display in communication with the processor.

* * * * *